(12) United States Patent
Yamamoto et al.

(10) Patent No.: US 8,663,990 B2
(45) Date of Patent: Mar. 4, 2014

(54) MEASUREMENT METHOD UTILIZING INTERNAL STANDARD SUBSTANCE

(75) Inventors: Naoyuki Yamamoto, Hyogo (JP); Tatsuo Kurosawa, Hyogo (JP)

(73) Assignee: Wako Pure Chemical Industries, Ltd., Osaka (JP)

( * ) Notice: Subject to any disclaimer, the term of this patent is extended or adjusted under 35 U.S.C. 154(b) by 81 days.

(21) Appl. No.: 13/318,079

(22) PCT Filed: Apr. 27, 2010

(86) PCT No.: PCT/JP2010/057466
§ 371 (c)(1),
(2), (4) Date: Oct. 28, 2011

(87) PCT Pub. No.: WO2010/126044
PCT Pub. Date: Nov. 4, 2010

(65) Prior Publication Data
US 2012/0043207 A1    Feb. 23, 2012

(30) Foreign Application Priority Data

Apr. 28, 2009   (JP) .................................. 2009-109635

(51) Int. Cl.
*G01N 27/26*    (2006.01)
*C07K 1/14*     (2006.01)
*C07K 1/26*     (2006.01)
*C07D 403/06*   (2006.01)

(52) U.S. Cl.
USPC ............... 436/8; 530/412; 204/451; 204/452; 548/364.7

(58) Field of Classification Search
None
See application file for complete search history.

(56) References Cited

U.S. PATENT DOCUMENTS

2003/0170734 A1    9/2003  Williams et al.
2009/0069546 A1 *  3/2009  Date et al. .................. 530/391.3

FOREIGN PATENT DOCUMENTS

| EP | 2006289 A1 * | 12/2008 |
| JP | 2003-034697 A | 2/2003 |
| JP | 2005-521885 A | 7/2005 |
| JP | 2007-024610 A | 2/2007 |

OTHER PUBLICATIONS

International Search Report of PCT/JP2010/057466, mailing date Aug. 3, 2010.

* cited by examiner

*Primary Examiner* — Shafiqul Haq
(74) *Attorney, Agent, or Firm* — Westerman, Hattori, Daniels & Adrian, LLP

(57) ABSTRACT

A subject of the present invention is to provide a measurement method using an internal standard substance in an electrophoresis where an analyte is a protein or a compound. The present invention relates to a measurement method for an analyte by an electrophoresis, characterized in that a peak of the analyte is identified by using as an internal standard substance (1) a combination of a compound I having 3 or more anion groups in a molecule and a compound II where 1 to 3 groups of the anion groups of said compound I have been substituted by cation groups, or (2) a combination of a compound III having 3 or more cation groups in a molecule and a compound IV where 1 to 3 groups of the cation groups of said compound III have been substituted by cation groups.

8 Claims, 2 Drawing Sheets

MEASUREMENT METHOD UTILIZING INTERNAL STANDARD SUBSTANCE

TECHNICAL FIELD

The present invention relates to a measurement method for an analyte using an internal standard substance.

BACKGROUND ART

In the capillary electrophoresis method, it has been carried out in the past to use one kind of internal standard substance and specify an approximate position of an analyte using a peak thereof as a tip marker (see Patent Literature 1). However, when only one kind of internal standard substance is used, positional relations among peaks of an internal standard substance and an analyte may be varied by influence of measurement conditions and impurities in a sample. Therefore, when position of an analyte is required to be specified with good accuracy, a molecular weight marker has been used.

When an analyte is DNA or RNA, it has been also known that measurement is carried out using two kinds of markers of high molecular weight side and low molecular weight side. The molecular weight marker to be used in this case is DNA or RNA, which are selected based on the number of base thereof. That is, when electrophoresis of DNA or RNA is carried out, molecular weight of the analyte has been able to be obtained from positional relations with two molecular weight markers by setting positions of the molecular weight markers accurately. However, the molecular weight marker to be used here is DNA, RNA, or the like which is labeled with an intercalator, and had such problems that stability was poor; the molecular weight marker reacted with a substance in a sample when a serum sample was used; background was increased; the molecular weight marker showed a broad peak; and the like.

On the other hand, when an analyte is a protein or a compound, since mobility of the analyte varies depending on molecular weight or electric charge of the analyte, usually only one kind of internal standard substance is used and purpose of the use was to specify an approximate position of the analyte. Therefore, in such case when a protein or a compound is measured, development of a measurement method which does not have such problems in the measurement of DNA or RNA as described above and is capable of specifying a protein or a compound with good accuracy has been presently demanded.

In particular, when electrophoresis is carried out using a fine capillary as in microchip electrophoresis, there has been such a problem that migration time of a substance could vary even under the same conditions if chip is changed to another one, because of the fineness of the capillary. For this reason, it was sometimes difficult to specify the target peak. Further, since a high sensitivity measurement becomes possible in the case of such measurement method, it was essential to use an internal standard substance which does not influence on the measurement and is capable of measuring with good sensitivity. Therefore, development of a measurement method which can specify a peak of a measurement substance under the conditions as described above has been also demanded.

PRIOR ART LITERATURES

Patent Literatures

Patent Literature 1: JP-A-2007-24610

DISCLOSURE OF INVENTION

Problem to be Solved by the Invention

A subject of the present invention is to provide a measurement method using an internal standard substance in an electrophoresis where an analyte is a protein or a compound.

Means for Solving the Problem

Under these circumstances, the present inventors have intensively studied for developing a measurement method by a capillary electrophoresis method using an internal standard substance when an analyte is a protein or a compound. As a result, the inventors have found that a peak of an analyte can be easily specified even when the analyte is a protein or a compound, by using as an internal standard substance a combination of a compound having 3 or more anion groups in a molecule and a compound where 1 to 3 anion groups of said compound have been substituted by cation groups, or a combination of a compound having 3 or more cation groups in a molecule and a compound where 1 to 3 cation groups of said compound have been substituted by anion groups. That is, in the capillary electrophoresis method where a substance is migrated in a direction from minus side to plus side, since a peak of a compound having 3 or more anion groups in a molecule is detected in an earlier time and a peak of a compound having 3 or more cation groups in a molecule is detected in a delayed time, by using a compound having 3 or more cation or anion groups in a molecule and a compound where 1 to 3 anion or cation groups of said compound have been substituted by the one having opposite electric charge, it becomes possible to adjust a peak of the analyte to be positioned between two peaks of the internal standard substances, thereby a peak of the analyte can be easily identified. Based on this finding, the present invention was completed.

That is, the present invention relates to

"a measurement method for an analyte by the capillary electrophoresis method, characterized in that a peak of the analyte is identified by using as an internal standard substance (1) a combination of a compound 1 having 3 or more anion groups in a molecule and a compound II where 1 to 3 groups of the anion groups of said compound I have been substituted by cation groups, or (2) a combination of a compound III having 3 or more cation groups in a molecule and a compound IV where 1 to 3 groups of the cation groups of said compound III have been substituted by cation groups".

Effects of the Invention

According to the present invention, it becomes possible to specify an analyte easily and with good accuracy even when there are plural neighboring peaks. In addition, since the labeling substance to be used here does not react with a substance in the sample or does not exert an influence such as increasing background and the like, it becomes possible to measure with good accuracy even in an analysis of a trace component.

BEST MODE FOR CARRYING OUT THE INVENTION

Figure 1:
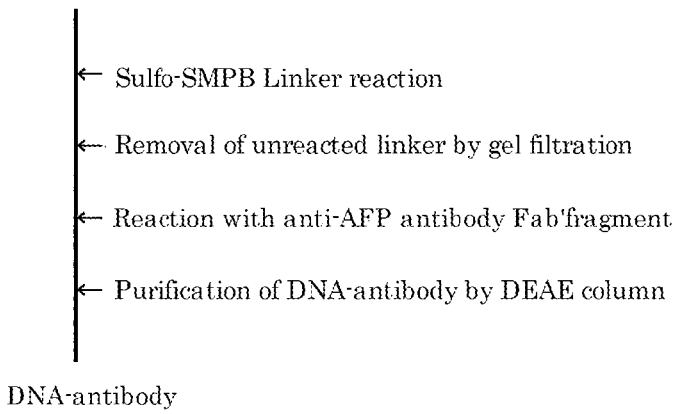
FIG. 1 is a drawing showing the method for preparing a DNA-labeled antibody in Example 1.

[Compound I Having 3 or More Anion Groups in a Molecule Relevant to the Present Invention (Hereinafter, Sometimes Abbreviated as Anion-Group-Containing Compound I Relevant to the Present Invention)]

The anion-group-containing compound I relevant to the present invention is a compound having usually 3 to 10 anion groups, preferably 5 to 8 anion groups, more preferably 5 to 6 anion groups, and particularly preferably 5 anion groups in a molecule. When electrophoresis is carried out in a direction from minus side to plus side, since migration velocity of such compound as described above becomes more rapid, a peak thereof is detected usually in an earlier time than that of any analytes, and thus, the compound can be used as a useful internal standard substance. The above-described anion group includes, for example, $-HPO_4^-$, $-NO_3^-$, $-ClO_4^-$, $-COO^-$ and $-SO_3^-$, and among them, $-COO^-$ and $-SO_3^-$ are preferable. $-COO^-$ is suitable for introducing a cation group due to its high reactivity. Since $-SO_3^-$ can increase fluorescence intensity, when the above-described anion-group-containing compound I relevant to the present invention is detected by fluorescence, it is preferable to have said group. It should be noted that specific example of the above-described anion group may be the one which becomes an anion group during an electrophoresis (during being dissolved in a migration solution), and may be an, acid bound to a hydrogen ion or a salt such as an alkali metal salt (for example, a lithium salt, a sodium salt, a potassium salt, a rubidium salt), an ammonium salt, an organic ammonium salt (for example, a trimethylammonium salt, a triethylammonium salt, a tripropylammonium salt), and the like.

Specific example of the anion-group-containing compound I relevant to the present invention includes, for example, a compound represented by the general formula [1] or a salt thereof:

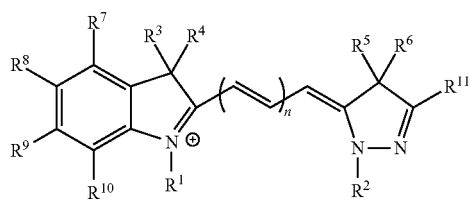

[1]

[wherein $R^1$ to $R^6$ each independently represent an alkyl group having, as a substituent, $-COO^-$ or $-SO_3^-$ or being unsubstituted, which may have an amide bond;
$R^7$ to $R^{10}$ each independently represent an alkyl group, an alkynyl group, an aryl group, an alkoxy group, an aryloxy group, an alkylsulfonyl group, an arylsulfonyl group, a substituted amino group, $-COO^-$, $-SO_3^-$, a halogen atom, a hydroxyl group, a cyano group or nitro group;
$R^{11}$ represents a hydrogen atom, an alkyl group, an alkynyl group or an aryl group; and n represents an integer from 0 to 3;
and 3 groups of $R^1$ to $R^{11}$ represent $-COO^-$ or $-SO_3^-$, or a group having, as a substituent, $-COO^-$ or $-SO_3^-$].

The above-described compound I represented by the general formula [1] or a salt thereof is a fluorescent substance having an excitation wavelength at around 635 nm, and also showing a sharp peak shape when migrated by a capillary electrophoresis, and hence it becomes a particularly useful internal standard substance in a capillary electrophoresis measurement by detecting fluorescence.

$-COO^-$ or $-SO_3^-$ as a substituent of an alkyl group represented by $R^1$ to $R^6$ in the general formula [1] and $-COO^-$ or $-SO_3^-$ represented by $R^7$ to $R^{10}$ may be a group which becomes an anion group during an electrophoresis (during being dissolved in a migration solution), and may be an acid bound to a hydrogen ion, such as carboxylic acid ($-COOH$), sulfonic acid ($-SO_3H$), or a salt such as an alkali metal salt (for example, a lithium salt, a sodium salt, a potassium salt, a rubidium salt), an ammonium salt, an organic ammonium salt (for example, a trimethylammonium salt, a triethylammonium salt, a tripropylammonium salt).

The alkyl group of an alkyl group having, as a substituent, $-COO^-$ or $-SO_3^-$ or being unsubstituted, which may have an amide bond, represented by $R^1$ to $R^6$ in the general formula [1] may be any of straight-chained, branched or cyclic one, but straight-chained one, having usually $C_1$ to $C_{10}$, preferably $C_1$ to $C_6$, and more preferably $C_1$ to $C_5$, is preferable. Specifically, the alkyl group includes, for example, a methyl group, an ethyl group, a n-propyl group, an isopropyl group, a n-butyl group, an isobutyl group, a sec-butyl group, a tert-butyl group, a n-pentyl group, an isopentyl group, a sec-pentyl group, a tert-pentyl group, a neopentyl group, a n-hexyl group, an isohexyl group, a sec-hexyl group, a tert-hexyl group, a neohexyl group, a n-heptyl group, an isoheptyl group, a sec-heptyl group, a tert-heptyl group, a neoheptyl group, a n-octyl group, an isooctyl group, a sec-octyl group, a tert-octyl group, a neooctyl group, a n-nonyl group, an isononyl group, a sec-nonyl group, a tert-nonyl group, a neononyl group, a n-decyl group, an isodecyl group, a sec-decyl group, a tert-decyl group, a neodecyl group, a cyclopropyl group, a cyclobutyl group, a cyclopentyl group, a cyclohexyl group, a cycloheptyl group, a cyclooctyl group, a cyclononyl group, a cyclodecyl group, and the like. Among them, for example, a straight-chained alkyl group such as a methyl group, an ethyl group, a n-propyl group, a n-pentyl group, is preferable.

The alkyl group of an alkyl group having, as a substituent, $-COO^-$ or $-SO_3^-$ or being unsubstituted, which may have an amide bond, represented by $R^1$ to $R^6$ includes a substituted or unsubstituted alkyl group which does not have an amide bond, or a substituted or unsubstituted alkyl group which has usually 1 to 10 amide bonds, preferably 1 to 3 amide bonds, and more preferably one amide bond in the alkyl chain thereof.

A preferable specific example of the unsubstituted alkyl group which may have an amide bond includes, for example, a group represented by the following general formula [59]:

  [59]

(wherein $R^{21}$ represents a hydrogen atom or an alkyl group; $T_1$ and k pieces of $T_2$ represent an alkylene group; and k represents an integer from 0 to 10).

The alkyl group represented by $R^{21}$ in the general formula [59] may be any of straight-chained, branched or cyclic one, having usually $C_1$ to $C_{10}$, and preferably $C_1$ to $C_6$. Specifically, the alkyl group includes, for example, a methyl group, an ethyl group, a n-propyl group, an isopropyl group, a n-butyl group, an isobutyl group, a sec-butyl group, a tert-butyl group, a neobutyl group, a n-pentyl group, an isopentyl group, a sec-pentyl group, a tert-pentyl group, a neopentyl group, a n-hexyl group, an isohexyl group, a sec-hexyl group, a tert-hexyl group, a neohexyl group, a n-heptyl group, an isoheptyl group, a sec-heptyl group, a tert-heptyl group, a neoheptyl group, a n-octyl group, an isooctyl group, a sec-octyl group, a tert-octyl group, a neooctyl group, a n-nonyl group, an isononyl group, a sec-nonyl group, a tert-nonyl group, a neo-nonyl group, a n-decyl group, an isodecyl group, a sec-decyl group, a tert-decyl group, a neodecyl group, a cyclopropyl group, a cyclobutyl group, a cyclopentyl group, a cyclohexyl group, a cycloheptyl group, a cyclooctyl group, a cyclononyl group, a cyclodecyl group, and the like.

The alkylene group represented by $T_1$ and k pieces of $T_2$ may be any of straight-chained, branched or cyclic one, having $C_2$ to $C_{10}$, and preferably $C_2$ to $C_8$. Specifically, the alkylene group includes, a straight-chained alkylene group such as, for example, a methylene group, an ethylene group, a trimethylene group, a tetramethylene group, a pentamethylene group, a hexamethylene group, a heptamethylene group, octamethylene group, a nonamethylene group, decamethylene group; a branched alkylene group such as, for example, an ethylidene group, a propylidene group, an isopropylidene group, a 1-methyltrimethylene group, a 2-methyltrimethylene group, a 1,1-dimethylethylene group, a 1,2-dimethylethylene group, an ethylethylene group, a 1-methyltetramethylene group, a 1,1-dimethyltrimethylene group, a 2,2-dimethyltrimethylene group, a 2-ethyltrimethylene group, a 1-methylpentamethylene group, a 2-methylpentamethylene group, a 1,3-dimethyltetramethylene group, a 3-ethyltetramethylene group, a 1-methylhexamethylene group, a 1-methylheptamethylene group, a 1,4-diethyltetramethylene group, a 2,4-dimethylheptamethylene group, a 1-methyloctamethylene group, a 1-methylnonamethylene group; and a cyclic alkylene group such as, for example, a cyclopropylene group, a 1,3-cyclobutylene group, a 1,3-cyclopentylene group, a 1,4-cyclohexylene group, a 1,5-cycloheptylene group, a 1,5-cyclooctylene group, a 1,5-cyclononylene group, a 1,6-cyclodecylene group.

k represents usually an integer from 0 to 10, preferably an integer from 0 to 3, and more preferably 0 or 1.

Among the specific examples of $R^1$ to $R^6$ in the above-described general formula [1], an alkyl group having, as a substituent, $-COO^-$ or $-SO_3^-$ or being unsubstituted is particularly preferable. As for more preferable specific examples, $R^1$ and $R^2$ each independently are an alkyl group having, as a substituent, $-COO^-$ or $-SO_3^-$, and more preferably an alkyl group having, as a substituent, $-COO^-$ or $-SO_3^-$ of $C_1$ to $C_5$. As for $R^3$ and $R^4$, either one thereof is an alkyl group having, as a substituent, $-COO^-$ or $-SO_3^-$, and preferably an alkyl group having, as a substituent, $-COO^-$ or $-SO_3^-$ of $C_1$ to $C_5$, and the other is an unsubstituted alkyl group, preferably an unsubstituted alkyl group of $C_1$ to $C_5$. As for $R^5$ and $R^6$, either one thereof is an alkyl group having, as a substituent, $-COO^-$ or $-SO_3^-$, and preferably an alkyl group having as a substituent $-COO^-$ or $-SO_3^-$ of $C_1$ to $C_5$, and the other is an unsubstituted alkyl group, preferably an unsubstituted alkyl group of $C_1$ to $C_5$.

The alkyl group represented by $R^7$ to $R^{10}$ in the general formula [1] may be any of straight-chained, branched or cyclic one of usually $C_1$ to $C_6$, and preferably $C_1$ to $C_3$. Specifically, the alkyl group includes, for example, a methyl group, an ethyl group, a n-propyl group, an isopropyl group, a n-butyl group, an isobutyl group, a sec-butyl group, a tert-butyl group, a n-pentyl group, an isopentyl group, a sec-pentyl group, a tert-pentyl group, a neopentyl group, a n-hexyl group, an isohexyl group, a sec-hexyl group, a tert-hexyl group, a neohexyl group, a cyclopropyl group, a cyclobutyl group, a cyclopentyl group, a cyclohexyl group, and the like.

The alkynyl group represented by $R^7$ to $R^{10}$ includes the one of usually $C_2$ to $C_6$, preferably $C_2$ to $C_4$, and specifically, for example, an ethynyl group, a 2-propynyl group, a 3-butynyl group, a 1-methyl-2-propynyl group, a 4-pentynyl group, a 2-methyl-4-pentynyl group, a 5-hexynyl group, and the like.

The aryl group represented by $R^7$ to $R^{10}$ includes the one of usually $C_6$ to $C_{10}$, and specifically, for example, a phenyl group, a naphthyl group, and the like.

The alkoxy group represented by $R^7$ to $R^{10}$ may be any of straight-chained, branched or cyclic one of usually $C_1$ to $C_6$, and preferable $C_1$ to $C_3$. Specifically, the alkoxy group includes, for example, a methoxy group, an ethoxy group, a n-propoxy group, an isopropoxy group, a n-butoxy group, an isobutoxy group, a sec-butoxy group, a tert-butoxy group, a n-pentyloxy group, an isopentyloxy group, a sec-pentyloxy group, a tert-pentyloxy group, a neopentyloxy group, a n-hexyloxy group, an isohexyloxy group, a sec-hexyloxy group, a tert-hexyloxy group, a neohexyloxy group, a cyclopropoxy group, a cyclopentyloxy group, a cyclohexyloxy group, and the like.

The aryloxy group represented by $R^7$ to $R^{10}$ includes the one of usually $C_6$ to $C_{10}$, and specifically, for example, a phenyloxy group, a naphthoxy group, and the like.

The alkylsulfonyl group of an alkylsulfonyl group represented by $R^7$ to $R^{10}$ includes a group where $-OH$ group of a sulfo group ($-SO_3OH$) has been substituted by an alkyl group, and may be any of straight-chained, branched or cyclic one of usually $C_1$ to $C_6$. Specifically, the alkylsulfonyl group includes, for example, a methylsulfonyl group, an ethylsulfonyl group, a n-propylsulfonyl group, an isopropylsulfonyl group, a n-butylsulfonyl group, an isobutylsulfonyl group, a sec-butylsulfonyl group, a tert-butylsulfonyl group, a n-pentylsulfonyl group, an isopentylsulfonyl group, a sec-pentylsulfonyl group, a tert-pentylsulfonyl group, a neopentylsulfonyl group, a n-hexylsulfonyl group, an isohexylsulfonyl group, a sec-hexylsulfonyl group, a tert-hexylsulfonyl group, a neohexylsulfonyl group, a cyclopropylsulfonyl group, a cyclobutylsulfonyl group, a cyclopentylsulfonyl group, a cyclohexylsulfonyl group, and the like.

The arylsulfonyl group represented by $R^7$ to $R^{10}$ includes a group where $-OH$ group of a sulfo group ($-SO_3OH$) has been substituted by an aryl group, and may be any of straight-chained, branched or cyclic one of usually $C_6$ to $C_{10}$. Specifically, the group includes, for example, a phenylsulfonyl group, a naphthylsulfonyl group, and the like.

The halogen atom represented by $R^7$ to $R^{10}$ includes, for example, a fluorine atom, a chlorine atom, a bromine atom, an iodine atom, and the like.

The substituted amino group represented by $R^7$ to $R^{10}$ includes a group where 1 or 2 hydrogen atoms of an amino group have been substituted by a substituent, and the substituent includes, for example, an alkyl group, an alkoxycarbonyl group, an acyl group, a sulfo group, and the like.

The alkyl group included as a substituent of the substituted amino group represented by $R^7$ to $R^{10}$ may be any of straight-chained, branched or cyclic one of usually $C_1$ to $C_{10}$, and preferably $C_1$ to $C_6$. Specifically, the group includes, for example, a methyl group, an ethyl group, a n-propyl group, an isopropyl group, a n-butyl group, an isobutyl group, a sec-butyl group, a tert-butyl group, a n-pentyl group, an isopentyl group, a sec-pentyl group, a tert-pentyl group, a neopentyl group, a n-hexyl group, an isohexyl group, a sec-hexyl group, a tert-hexyl group, a neohexyl group, a n-heptyl group, an isoheptyl group, a sec-heptyl group, a tert-heptyl group, a neoheptyl group, a n-octyl group, an isooctyl group, a sec-octyl group, a tert-octyl group, a neooctyl group, a n-nonyl group, an isononyl group, a sec-nonyl group, a tert-nonyl group, a neononyl group, a n-decyl group, an isodecyl group, a sec-decyl group, a tert-decyl group, a neodecyl group, a cyclopropyl group, a cyclobutyl group, a cyclopentyl group, a cyclohexyl group, a cycloheptyl group, a cyclooctyl group, a cyclononyl group, a cyclodecyl group, and the like.

The alkoxycarbonyl group included as a substituent of the substituted amino group represented by $R^7$ to $R^{10}$ may be any of straight-chained, branched or cyclic one of usually $C_1$ to $C_{10}$, and preferably $C_1$ to $C_6$. Specifically, the group includes, for example, a methoxycarbonyl group, an ethoxycarbonyl group, a n-propoxycarbonyl group, an isopropoxycarbonyl group, a n-butoxycarbonyl group, an isobutoxycarbonyl group, a sec-butoxycarbonyl group, a tert-butoxycarbonyl group, a n-pentyloxycarbonyl group, an isopentyloxycarbonyl group, a sec-pentyloxycarbonyl group, a tert-pentyloxycarbonyl group, a neopentyloxycarbonyl group, a n-hexyloxycarbonyl group, an isohexyloxycarbonyl group, a sec-hexyloxycarbonyl group, a tert-hexyloxycarbonyl group, a neohexyloxycarbonyl group, a n-heptyloxycarbonyl group, an isoheptyloxycarbonyl group, a sec-heptyloxycarbonyl group, a tert-heptyloxycarbonyl group, a neoheptyloxycarbonyl group, a n-octyloxycarbonyl group, an isooctyloxycarbonyl group, a sec-octyloxycarbonyl group, a tert-octyloxycarbonyl group, a neooctyloxycarbonyl group, a n-nonyloxycarbonyl group, an isononyloxycarbonyl group, a sec-nonyloxycarbonyl group, a tert-nonyloxycarbonyl group, a neononyloxycarbonyl group, a n-decyloxycarbonyl group, an isodecyloxycarbonyl group, a sec-decyloxycarbonyl group, a tert-decyloxycarbonyl group, a neodecyloxycarbonyl group, a cycloporpoxycarbonyl group, a cyclobutoxycarbonyl group, a cyclopentyloxycarbonyl group, a cyclohexyloxycarbonyl group, a cycloheptyloxycarbonyl group, a cyclooctyloxycarbonyl group, a cyclononyloxycarbonyl group, a cyclodecyloxycarbonyl group, and the like.

The acyl group included as a substituent of the substituted amino group represented by $R^7$ to $R^{10}$ includes, for example, a group derived from an aliphatic carboxylic acid, a group derived from an aromatic carboxylic acid, and the like.

Said acyl group derived from an aliphatic carboxylic acid may be any of straight-chained, branched or cyclic one, and may further have a double bond in a chain, and has usually $C_2$ to $C_{20}$, preferably $C_2$ to $C_{15}$, more preferably $C_2$ to $C_{10}$, and further more preferably $C_2$ to $C_6$. Specifically, the group includes, for example, an acetyl group, a propionyl group, a butyryl group, an isobutyryl group, a valeryl group, an isovaleryl group, a pivaloyl group, a hexanoyl group, a heptanoyl group, an octanoyl group, a decanoyl group, a lauroyl group, a myristoyl group, a palmitoyl group, a stearoyl group, an icosanoyl group, an acryloyl group, a methacryloyl group, a crotonoyl group, an oleoyl group, and the like.

Said acyl group derived from an aromatic carboxylic acid includes a group of usually $C_7$ to $C_{15}$, and preferable $C_7$ to $C_{11}$, and specifically, for example, a benzoyl group, a naphthoyl group, an anthoyl group, and the like.

Among the specific examples of $R^7$ to $R^{10}$ in the above-described general formula [1], —COO⁻ or —SO$_3$⁻ or a hydrogen atom is particularly preferable. More preferable specific examples are a case where 3 groups of $R^7$ to $R^{10}$ are hydrogen atoms and one remainder is —COO⁻ or —SO$_3$⁻, and preferably —SO$_3$⁻.

The alkyl group represented by $R^{11}$ in the general formula [1] may be any of straight-chained, branched or cyclic one, and preferably straight-chained one, and has usually $C_1$ to $C_{10}$, preferably $C_1$ to $C_6$, and more preferably $C_1$ to $C_3$. Specifically, the group includes, for example, a methyl group, an ethyl group, a n-propyl group, an isopropyl group, a n-butyl group, an isobutyl group, a sec-butyl group, a tert-butyl group, a n-pentyl group, an isopentyl group, a sec-pentyl group, a tert-pentyl group, a neopentyl group, a n-hexyl group, an isohexyl group, a sec-hexyl group, a tert-hexyl group, a neohexyl group, a n-heptyl group, an isoheptyl group, a sec-heptyl group, a tert-heptyl group, a neoheptyl group, a n-octyl group, an isooctyl group, a sec-octyl group, a tert-octyl group, a neooctyl group, a n-nonyl group, an isononyl group, a sec-nonyl group, a tert-nonyl group, a neononyl group, a n-decyl group, an isodecyl group, a sec-decyl group, a tert-decyl group, a neodecyl group, a cyclopropyl group, a cyclobutyl group, a cyclopentyl group, a cyclohexyl group, a cycloheptyl group, a cyclooctyl group, a cyclononyl group, a cyclodecyl group, and the like.

The alkynyl group represented by $R^{11}$ includes a group of usually $C_2$ to $C_6$, and preferably $C_2$ to $C_4$, and specifically, for example, an ethynyl group, a 2-propynyl group, a 3-butynyl group, a 1-methyl-2-propynyl group, 4-pentynyl group, a 2-methyl-4-pentynyl group, a 5-hexynyl group, and the like.

The aryl group represented by $R^{11}$ includes a group of usually $C_6$ to $C_{10}$, and specifically, for example, a phenyl group, a naphthyl group, and the like.

Among specific examples of $R^{11}$ in the above-described general formula [1], an alkyl group is particularly preferable.

n in the general formula [1] represents usually an integer from 0 to 3, preferably 1 or 2, and more preferably 2.

At least 3 groups of $R^1$ to $R^{11}$ in the general formula [1] are —COO⁻ or —SO$_3$⁻, or a group having, as a substituent, —COO⁻ or —SO$_3$⁻, and a case where at least one group is —COO⁻ or a group having as a substituent —COO⁻ and at least two groups are —SO$_3$⁻ or a group having, as a substituent, —SO$_3$⁻ is preferable, and a case where at least one group is —COO⁻ or a group having, as a substituent, —COO⁻ and four groups are —SO$_3$⁻ or a group having, as a substituent, —SO$_3$⁻ is particularly preferable.

Among the compound I represented by the formula [1] of the present invention, for example, a compound represented by the following general formula [1a]:

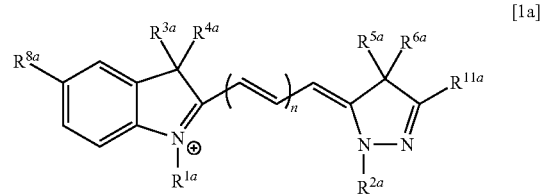

(wherein $R^{1a}$ to $R^{6a}$ each independently represent an alkyl group having, as a substituent, —COO⁻ or —SO$_3$⁻, or being unsubstituted; $R^{8a}$ represents —SO$_3$⁻, $R^{11a}$ represents an alkyl group; n represents the same as above; and two groups of $R^{1a}$ to $R^{6a}$ are —COO⁻ or —SO$_3$⁻, or a group having, as a substituent, —COO⁻ or —SO$_3$) is preferable.

The alkyl group of an alkyl group having, as a substituent, —COO⁻ or —SO$_3$⁻, or being unsubstituted represented by $R^{1a}$ to $R^{6a}$ in the general formula [1a] includes the same groups as exemplified for the aforementioned alkyl group of a substituted or unsubstituted alkyl group which may have an amide bond represented by $R^1$ to $R^6$ in the general formula [1], and preferable groups are the same as above.

As for $R^{1a}$ and $R^{2a}$, alkyl groups each independently having, as a substituent, $-COO^-$ or $-SO_3^-$ are preferable, and alkyl groups having, as a substituent, $-COO^-$ or $-SO_3^-$ of $C_1$ to $C_5$ are more preferable.

$R^{3a}$ and $R^{4a}$ are alkyl groups each independently having, as a substituent, $-COO^-$ or $-SO_3^-$, or being unsubstituted. Among these groups, a case where either one thereof is an alkyl group having, as a substituent, $-COO^-$ or $-SO_3^-$, and the other is an unsubstituted alkyl group is preferable, and a case where either one thereof is an alkyl group having, as a substituent, $-COO^-$ or $-SO_3^-$ of $C_1$ to $C_5$, and the other is an unsubstituted alkyl group of $C_1$ to $C_5$ is more preferable.

$R^{5a}$ and $R^{6a}$ are alkyl groups each independently having, as a substituent, $-COO^-$ or $-SO_3^-$, or being unsubstituted. Among these groups, a case where either one thereof is an alkyl group having, as a substituent, $-COO^-$ or $-SO_3^-$, and the other is an alkyl group is preferable, and a case where either one thereof is an alkyl group of $C_1$ to $C_5$ having, as a substituent, $-COO^-$ or $-SO_3^-$, and the other is an alkyl group of $C_1$ to $C_s$ is more preferable.

The alkyl group represented by $R^{11a}$ includes the same groups as exemplified for the aforementioned alkyl group represented by $R^{11}$ in the general formula [1], and preferable groups are the same as above.

At least two groups of $R^{1a}$ to $R^{6a}$ in the general formula [1a] are $-COO^-$ or $-SO_3^-$, or groups having, as a substituent, $-COO^-$ or $-SO_3^-$, and a case where at least one group is $-COO^-$ or a group having, as a substituent, $-COO^-$ and at least one group is $-SO_3^-$ or a group having, as a substituent, $-SO_3^-$ is preferable, and a case where one group is $-COO^-$ or a group having, as a substituent, $-COO^-$ and three groups are $-SO_3^-$ or groups having as a substituent $-SO_3^-$ is particularly preferable.

Preferable specific example of the compound I represented by the general formula [1] includes, for example, the following compounds:

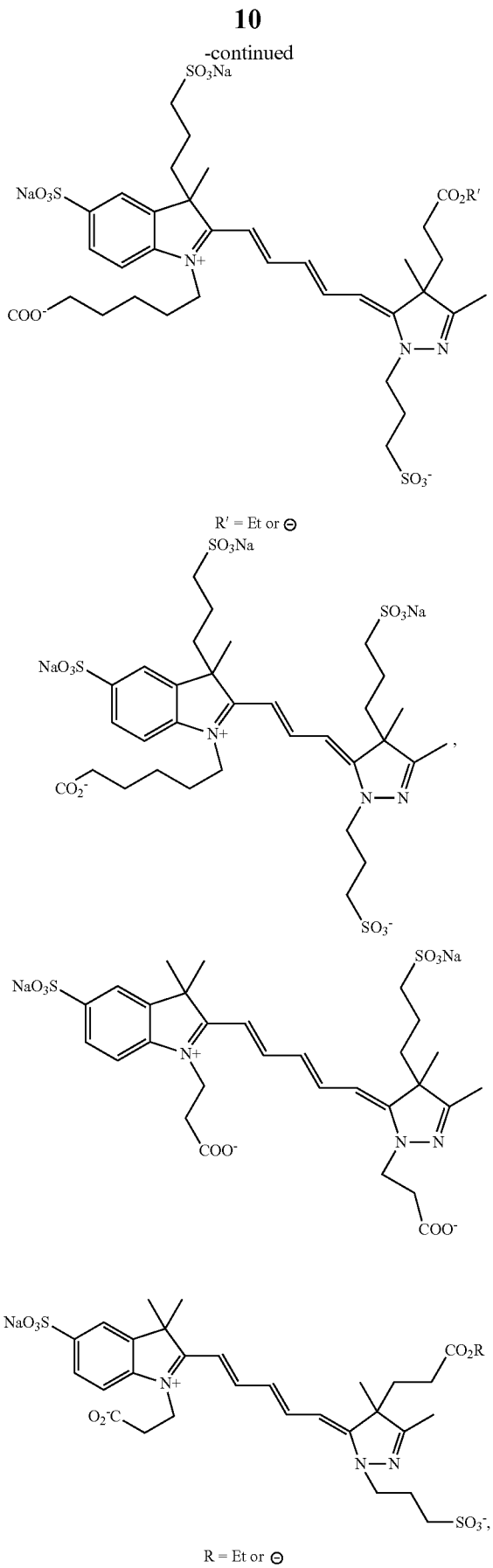

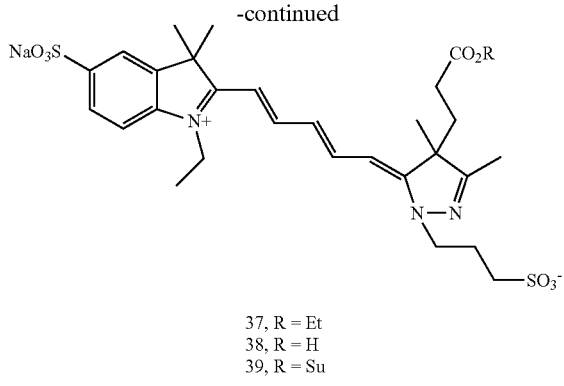

37, R = Et
38, R = H
39, R = Su and among them, the following compound:

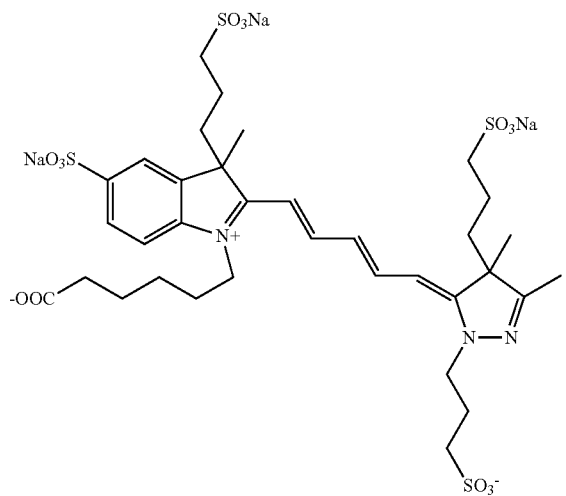

is preferable.

[Synthesis Method of the Anion-Group-Containing Compound I Relevant to the Present Invention]

The above-described general formula [1] can be appropriately synthesized, for example, according to the method described in WO 2007/114398.

[The Compound II where 1 to 3 Groups of Anion Group of Anion-Group-Containing Compound I Relevant to the Present Invention have been Substituted by Cation Groups (Hereinafter, Sometimes Abbreviated as the Cation-Group-Introduced Compound II Relevant to the Present Invention)]

The cation-group-introduced compound II relevant to the present invention has the same skeleton as that of the anion-group-containing compound I relevant to the present invention, where 1 to 3 groups, and preferably 1 to 2 groups of the anion groups have been substituted by cation groups. Due to this structure, when this compound II is electrophretically migrated in a direction from minus side to plus side, it becomes possible to delay a migration time of this compound II than that of the anion-group-containing compound I relevant to the present invention. That is, when the compound I where 1 to 3 anion groups have been substituted by cation groups depending on the migration time of an analyte and the anion-group-containing II compound relevant to the present invention are used as internal standard substances in an appropriately combined state, it becomes possible that a peak of the analyte is allowed to be positioned between peaks of the two internal standard substances.

Specific example of the above-described cation group includes a group represented by the following general formula [103]:

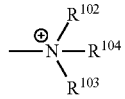

[103]

(wherein $R^{102}$ to $R^{104}$ each independently represent a hydrogen atom or an alkyl group of $C_1$ to $C_3$; and 2 to 3 groups of $R^{102}$ to $R^{104}$ together with a nitrogen atom to which they are bound may form a heterocyclic ammonium cation).

The alkyl group of $C_1$ to $C_3$ represented by $R^{102}$ to $R^{104}$ in the group represented by the general formula [103] may be any of straight-chained or branched one, and is preferably straight-chained one. Specifically, the alkyl group includes, for example, a methyl group, an ethyl group, a n-propyl group, an isopropyl group, and the like. Among them, a methyl group and an ethyl group are preferable, and a methyl group is more preferable.

The heterocyclic ammonium cation group which is formed by 2 to 3 groups of $R^{102}$ to $R^{104}$ together with a nitrogen atom to which they are bound includes, for example, a pyridinio group, a piperidinio group, and a pyridinio group substituted by an alkyl group of $C_1$ to $C_3$.

Specific example of the group represented by the general formula [103] includes, for example, a diethylammonium group, a dimethylammonium group, a methylethylammonium group, a trimethylammonium group, a triethylammonium group, a diethylmethylammonium group, an ethyldimethylammonium group, a pyridinio group, a piperidinio group, an N-methylpiperidinium group, an N-ethylpiperidinium group, an N-n-propylpiperidinium group, an N-isopropylpiperidinium group, and the like. Among them, a diethylammonium group and a dimethylammonium group are preferable, and a dimethylammonium group is more preferable.

Specific example of the group containing the general formula [103] in the terminal includes a group represented by the following general formula [101]:

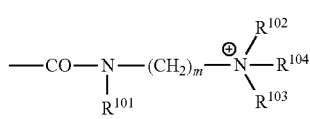

[101]

(wherein $R^{101}$ to $R^{104}$ are the same as above). The group represented by the general formula [101] can be obtained, for example, by reacting —COO— with a compound represented by the following general formula [102]:

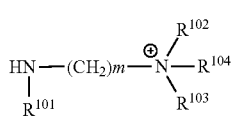

[102]

(wherein $R^{101}$ to $R^{104}$ are the same as above; and m represents an integer from 2 to 6), and by reacting in such way, the anion group can be substituted to the cation group.

The alkyl group of an alkyl group of $C_1$ to $C_3$ represented by $R^{101}$ to $R^{104}$ in the general formulas [101] and [102] is the same as that of an alkyl group of $C_1$ to $C_3$ represented by $R^{102}$ to $R^{104}$ in the above-described general formulas [103], and preferable groups are the same as above.

The heterocyclic ammonium cation group formed by 2 to 3 groups of $R^{102}$ to $R^{104}$ together with a nitrogen atom to which they are bound includes, for example, a pyridinio group, a piperidinio group, a pyperidinio group substituted by an alkyl group of $C_1$ to $C_3$ such as, for example, an N-methylpyperidinio group, an N-ethylpyperidinio group, an N-n-propylpyperidinio group, an N-isopropylpyperidinio group.

m in the general formulas [101] and [102] is usually 2 to 6, preferably 2 to 4, and particularly preferably 2.

Preferable specific example of a group represented by the general formula [101] includes, for example, a dimethylammonioethylcarbamoyl group, a trimethylammonioethylcarbamoyl group, a diethylammonioethylcarbamoyl group, a triethylammonioethylcarbamoyl group, a dimethylammoniopropylcarbamoyl group, a trimethylammoniopropylcarbamoyl group, a diisopropylammoniopropylcarbamoyl group, a triisopropylammoniopropylcarbamoyl group, a pyridinioethylcarbamoyl group, a pyridiniopropylcarbamoyl group, a methylpiperidinioethylcarbamoyl group, a methylpiperidiniopropylcarbamoyl group, an ethylpiperidinioethylcarbamoyl group, an ethylpiperidiniopropylcarbamoyl group, and the like. Among them, a dimethylammonioethylcarbamoyl group and a diethylammonioethylcarbamoyl group are preferable, further a dimethylammonioethylcarbamoyl group is more preferable.

The cation-group-introduced compound II relevant to the present invention includes, for example, a compound II' represented by the general formula [1'] or a salt thereof:

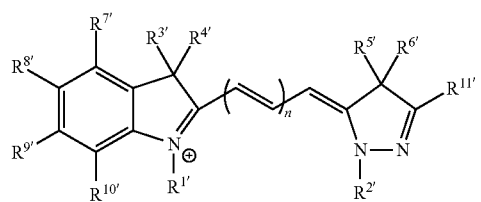

[1']

[wherein $R^{1'}$ to $R^{6'}$ each independently represent an alkyl group having as a substituent a group represented by the general formula [101]:

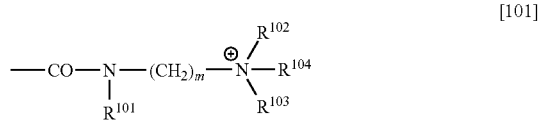

[101]

(wherein $R^{101}$ to $R^{104}$ each independently represent a hydrogen atom or an alkyl group of $C_1$ to $C_3$; and m represents an integer from 2 to 6), or an alkyl group having as a substituent $-COO^-$ or $-SO_3^-$, or being unsubstituted, which may have an amide bond;

$R^{7'}$ to $R^{10'}$ each independently represent an alkyl group, an alkynyl group, an aryl group, an alkoxy group, an aryloxy group, an alkylsulfonyl group, an arylsulfonyl group, a substituted amino group, $-COO^-$, $-SO_3^-$, a halogen atom, a hydrogen atom, a hydroxyl group, a cyano group or a nitro group;

$R^{11'}$ represents a hydrogen atom, an alkyl group, an alkynyl group or an aryl group; n represents an integer from 0 to 3.

At least one of $R^{1'}$ to $R^{6'}$ is an alkyl group having, as a substituent, a group represented by the general formula [101]].

The above-described compound II' represented by the general formula [1'] or a salt thereof is a fluorescent substance having an excitation wavelength at around 635 nm, and also showing a sharp peak shape when migrated by a capillary electrophoresis, and hence it becomes a particularly useful internal standard substance in a capillary electrophoresis measurement by detecting fluorescence.

$-COO^-$ or $-SO_3^-$ as a substituent of an alkyl group represented by $R^{1'}$ to $R^{6'}$ in the general formula [1'] and $-COO^-$ or $-SO_3^-$ represented by $R^{7'}$ to $R^{10'}$ may be a group which becomes an anion group during an electrophoresis (during being dissolved in a migration solution), and may be an acid bound to a hydrogen ion such as carboxylic acid ($-COOH$), sulfonic acid ($-SO_3H$) or a salt such as an alkali metal salt (for example, a lithium salt, a sodium salt, a potassium salt, a rubidium salt), an ammonium salt, an organic ammonium salt (for example, a trimethylammonium salt, a triethylammonium salt, a tripropylammonium salt), and the like.

The alkyl group of an alkyl group having, as a substituent, a group represented by the general formula [101] and an alkyl group having, as a substituent, $-COO^-$ or $-SO_3^-$ or being unsubstituted which may have an amide bond, represented by $R^{1'}$ to $R^{6'}$ in the general formula [1'] includes the same groups as the alkyl group of an alkyl group having, as a substituent, $-COO^-$ or $-SO_3^-$ or being unsubstituted which may have an amide bond, represented by $R^1$ to $R^6$ in the general formula [1], and preferable groups are the same as above.

Preferable specific example of $R^{1'}$ to $R^{6'}$ in the general formula [1'] includes an alkyl group having, as a substituent, a group represented by the general formula [101], or an alkyl group having, as a substituent, $-COO^-$ or $-SO_3^-$ or being unsubstituted. More preferable specific examples of $R^{1'}$ and $R^{2'}$ are a case where either one thereof is an alkyl group having, as a substituent, $-COO^-$ or $-SO_3^-$, preferably an alkyl group having, as a substituent, $-SO_3^-$, and more preferably an alkyl group of $C_1$ to $C_3$ having, as a substituent, $-SO_3^-$, and the other is an alkyl group having, as a substituent, a group represented by the general formula [101], and preferably an alkyl group of $C_1$ to $C_5$ having, as a substituent, a group represented by the general formula [101]. More preferable specific examples of $R^{3'}$ and $R^{4'}$ are a case where either one thereof is an alkyl group having, as a substituent, $-COO^-$ or $-SO_3^-$, preferably an alkyl group of $C_1$ to $C_5$ having, as a substituent, $-COO^-$ or $-SO_3^-$, and the other is an unsubstituted alkyl group, preferably an unsubstituted alkyl group of $C_1$ to $C_5$. More preferable specific examples of $R^{5'}$ and $R^{6'}$ are a case where either one thereof is an alkyl group having, as a substituent, $-COO^-$ or $-SO_3^-$, preferably an alkyl group of $C_1$ to $C_5$ having, as a substituent, $-COO^-$ or $-SO_3^-$, and the other is an unsubstituted alkyl group, preferably an unsubstituted alkyl group of $C_1$ to $C_5$.

Specific example and preferable one of the alkyl group, the alkynyl group, the aryl group, the alkoxy group, the aryloxy group, the alkylsulfonyl group, the arylsulfonyl group, the substituted amino group, $-COO^-$, $-SO_3^-$, the halogen atom represented by $R^{7'}$ to $R^{10'}$ in the general formula [1'] are the same as those described for $R^7$ to $R^{10}$ in the general formula [1], respectively. In addition, preferable specific example of $R^{7'}$ to $R^{10'}$ in the general formula [1'] includes $-COO^-$, $-SO_3^-$ or a hydrogen atom. More preferable specific example is a case where 3 groups of $R^{7'}$ to $R^{10'}$ are hydrogen atoms, and one remainder is —COO⁻ or —SO₃⁻, preferably —SO₃⁻.

Specific examples and preferable one of the alkyl group, the alkynyl group, and the aryl group represented by $R^{11'}$ in the general formula [1'] are the same as described for in the general formula [1]. In addition, preferable specific example of $R^{11'}$ in the general formula [1'] includes an alkyl group.

n in the general formula [1'] is usually an integer from 0 to 3, preferably 1 or 2, and more preferably 2.

In the general formula [1'], at least one of $R^{1'}$ to $R^{6'}$ is an alkyl group having, as a substituent, a group represented by the general formula [101], and preferably one of $R^{1'}$ to $R^{6'}$ is an alkyl group having, as a substituent, a group represented by the general formula [101], and particularly preferably $R^{1'}$ is an alkyl group having, as a substituent, a group represented by the general formula [101]. It should be noted that when the anion-group-containing compound I relevant to the present invention is a compound represented by the general formula [1] and contains an alkyl group having, as a substituent, —COO⁻, preferably the -COO⁻ is substituted by a group represented by the general formula [101] to convert to an alkyl group having, as a substituent, a group represented by the general formula [101].

In the general formula [1'], preferably at least 2 groups of $R^{1'}$ to $R^{11'}$ are —COO⁻ or

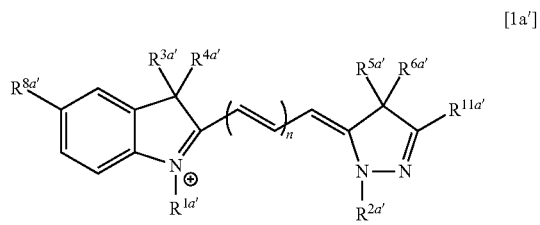

[1a']

—SO₃⁻, or a group having, as a substituent, —COO⁻ or —SO₃⁻, more preferably 3 groups are —COO⁻ or —SO₃⁻, or a group having, as a substituent, —COO⁻ or —SO₃⁻, and particularly preferably 3 groups are —SO₃⁻, or a group having, as a substituent, this group.

Among the compound II' represented by the general formula [1'] relevant to the present invention, for example, the compound represented by the following general formula [1a']:
(wherein $R^{1a'}$ to $R^{6a'}$ each independently represent an alkyl group having, as a substituent, a group represented by the general formula [101]:

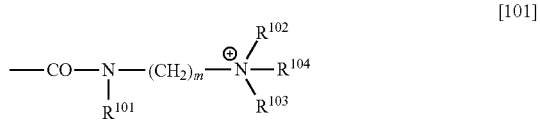

[101]

(wherein $R^{101}$ to $R^{104}$ are the same as above), or an alkyl group having as a substituent —COO⁻ or —SO₃⁻, or being unsubstituted, which may have an amide bond;

$R^{8a'}$ represents —SO₃⁻; $R^{11a'}$ represents an alkyl group; m is the same as above.

At least one of $R^{1a'}$ to $R^{6a'}$ is an alkyl group having, as a substituent, a group represented by the general formula [101]) is preferable.

The alkyl group of an alkyl group having, as a substituent, a group represented by the general formula [101], or an alkyl group having, as a substituent, —COO⁻ or —SO₃⁻, or being unsubstituted which may have an amide bond, represented by $R^{1a'}$ to $R^{6a'}$ in the general formula [1a'] includes the same group as the alkyl group of an alkyl group having, as a substituent, —COO⁻ or —SO₃⁻, or being unsubstituted which may have an amide bond, represented by $R^{1'}$ to $R^{6'}$ in the general formula [1'], and preferable group is the same as above.

Preferable examples of $R^{1a'}$ and $R^{2a'}$ are a case where either one thereof is an alkyl Group having, as a substituent, —COO⁻ or —SO₃⁻, preferably an alkyl group having, as a substituent, —SO₃⁻, and the other is an alkyl group having, as a substituent, a group represented by the general formula [101], and more preferable examples are a case where either one thereof is an alkyl group of $C_1$ to $C_5$ having, as a substituent, —SO₃⁻, and the other is an alkyl group having as a substituent a group of $C_1$ to $C_5$ represented by the general formula [101].

$R^{3a'}$ and $R^{4a'}$ each independently represent an alkyl group having, as a substituent, —COO⁻ or —SO₃⁻ or being unsubstituted. Among them, preferable examples are a case where either one thereof is an alkyl group having, as a substituent, —COO⁻ or —SO₃⁻ and the other is an unsubstituted alkyl group, and more preferable examples are a case where either one thereof an alkyl group of $C_1$ to $C_5$ having, as a substituent, —COO⁻ or —SO₃⁻, and the other is an unsubstituted alkyl group of $C_1$ to $C_5$.

$R^{5a'}$ and $R^{6a'}$ each independently represent an alkyl group having, as a substituent, —COO⁻ or —SO₃⁻ or being unsubstituted. Among them, preferable examples are a case where either one thereof is an alkyl group having, as a substituent, —COO⁻ or —SO₃⁻ and the other is an unsubstituted alkyl group, and more preferable examples are a case where either one thereof is an alkyl group of $C_1$ to $C_5$ having, as a substituent, —COO⁻ or —SO₃⁻, and the other is an unsubstituted alkyl group of $C_1$ to $C_5$.

The alkyl group represented by $R^{11a'}$ includes the same group as exemplified for an alkyl group represented by $R^{11}$ in the aforementioned general formula [1], and preferable group is the same as above.

In the general formula [1a'], at least one group of $R^{1a'}$ to $R^{6a'}$ is an alkyl group having, as a substituent, a group represented by the general formula [101], and preferably at least $R^{1a'}$ is an alkyl group having, as a substituent, a group represented by the general formula [101].

In the general formula [1a'], preferably at least one group of $R^{1a'}$ to $R^{6a'}$ is —COO⁻ or —SO₃⁻, or an alkyl group having, as a substituent, —COO⁻ or —SO₃⁻, more preferably two groups are —COO⁻ or —SO₃⁻, or alkyl groups having, as a substituent, —COO⁻ or —SO₃⁻, and particularly preferably two groups are —SO₃⁻, or alkyl groups having, as a substituent, this group.

n in the general formula [1a'] is usually an integer from 0 to 3, and preferably 1 or 2.

Preferable specific example of the general formula [1'] includes, for example, the following compounds:

17
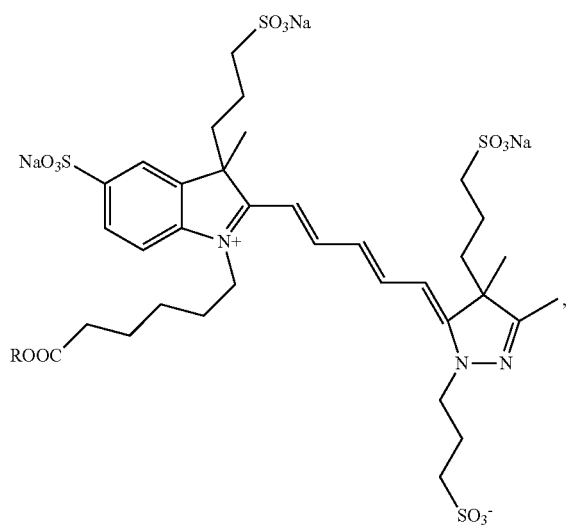
R: NHCH$_2$CH$_2$N$^+$HMe$_2$
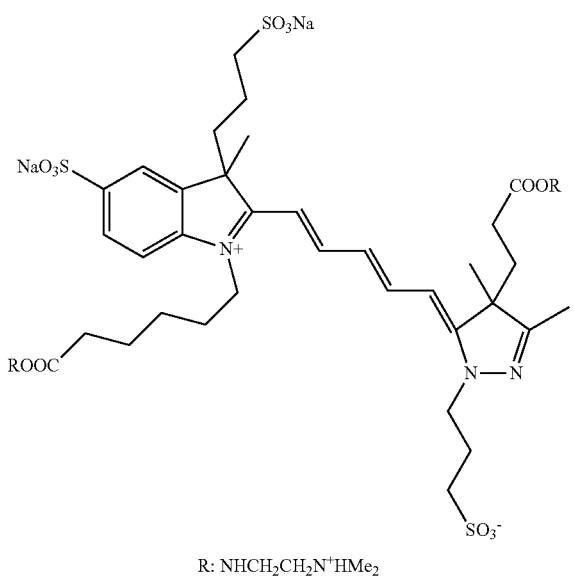
R: NHCH$_2$CH$_2$N$^+$HMe$_2$
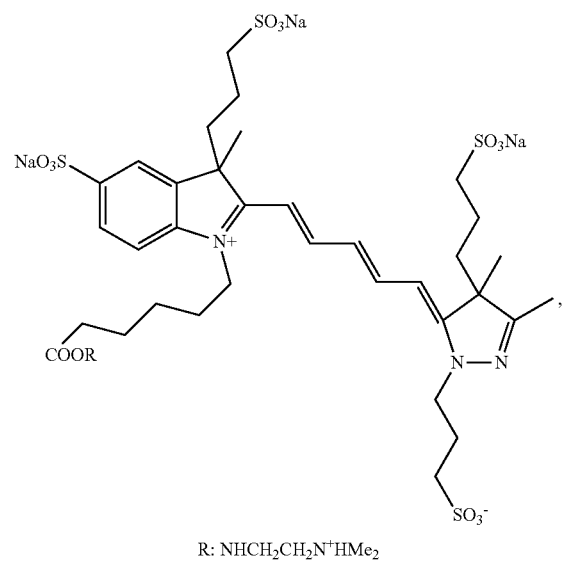
R: NHCH$_2$CH$_2$N$^+$HMe$_2$
18
-continued
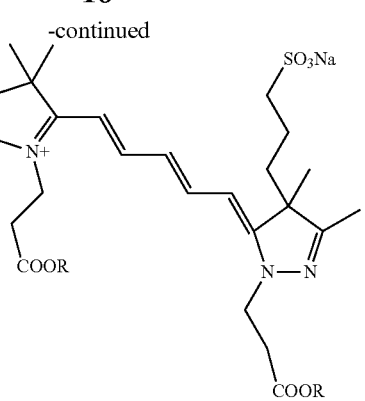
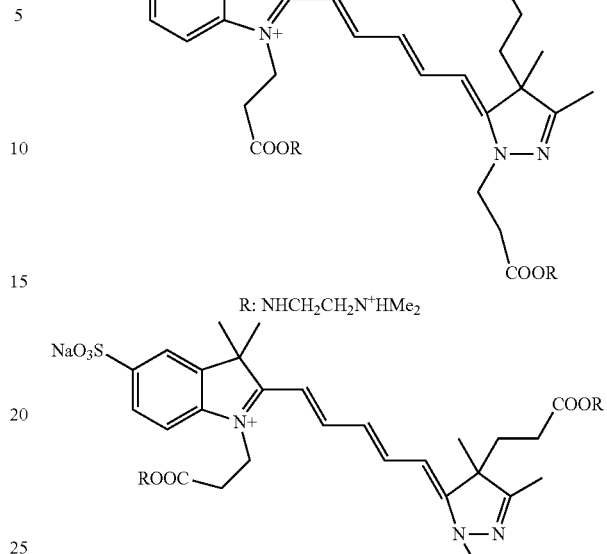
R: NHCH$_2$CH$_2$N$^+$HMe$_2$
R: NHCH$_2$CH$_2$N$^+$HMe$_2$
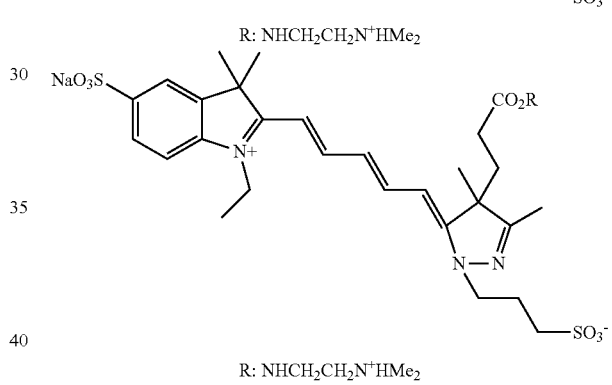
R: NHCH$_2$CH$_2$N$^+$HMe$_2$
and among them, the following compound:
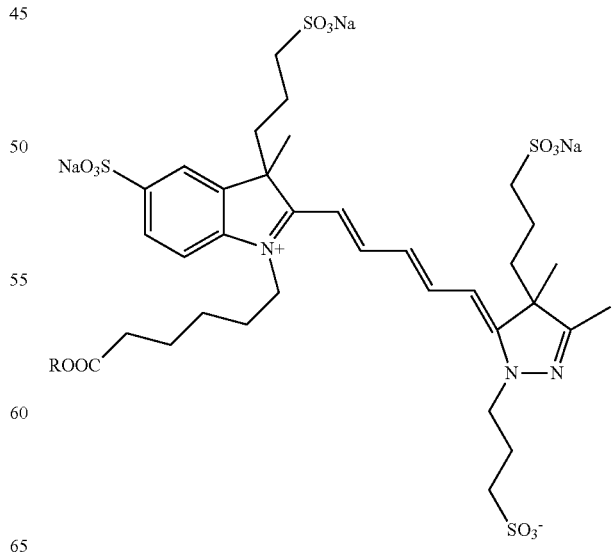
R: NHCH$_2$CH$_2$NMe$_2$
is preferable.

[Synthesis Method of the Cation-Group-Introduced Compound II' Relevant to the Present Invention]

The compound II' represented by the general formula [1'] can be synthesized, for example, using an indolenine compound and a pyrazole compound according to the following method.

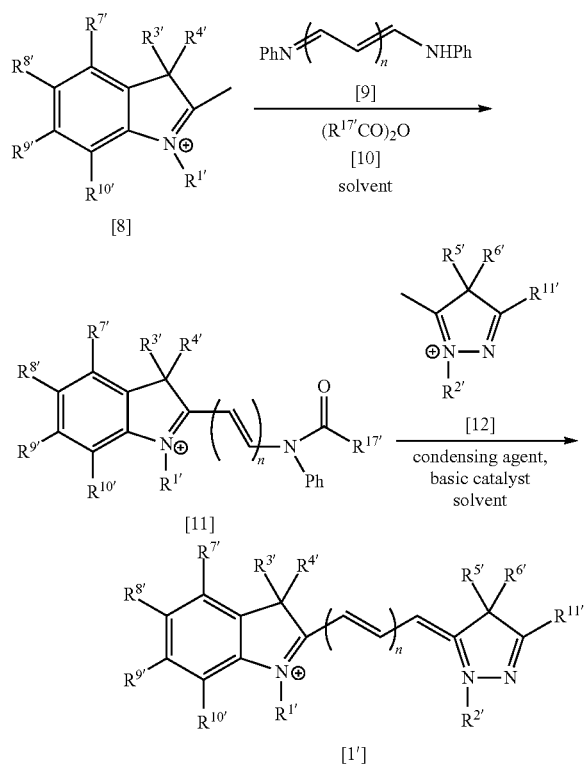

(wherein $R^{17'}$ represents an alkyl group or an aryl group; $R^{1'}$ to $R^{11'}$ and n represent the same as above).

In the general formulas [10] and [11], the alkyl group represented by $R^{17'}$ may be any of straight-chained, branched or cyclic one of usually $C_1$ to $C_{10}$, and preferably $C_1$ to $C_3$. Specifically, the alkyl group includes, for example, a methyl group, an ethyl group, a n-propyl group, an isopropyl group, a n-butyl group, an isobutyl group, a sec-butyl group, a tert-butyl group, a n-pentyl group, an isopentyl group, a sec-pentyl group, a tert-pentyl group, a neopentyl group, a n-hexyl group, an isohexyl group, a sec-hexyl group, a tert-hexyl group, a neohexyl group, a n-heptyl group, an isoheptyl group, a sec-heptyl group, a tert-heptyl group, a neoheptyl group, a n-octyl group, an isooctyl group, a sec-octyl group, a tert-octyl group, a neooctyl group, a n-nonyl group, an isononyl group, a sec-nonyl group, a tert-nonyl group, a neononyl group, a n-decyl group, an isodecyl group, a sec-decyl group, a tert-decyl group, a neodecyl group, a cyclopropyl group, a cyclobutyl group, a cyclopentyl group, a cyclohexyl group, a cycloheptyl group, a cyclooctyl group, a cyclononyl group, a cyclodecyl group, and the like.

The aryl group represented by $R^{17'}$ includes the one of usually $C_6$ to $C_{10}$, and specifically, for example, a phenyl group, a naphthyl group, and the like.

That is, firstly an indolenine compound represented by the general formula [8] (indolenine structure part), a compound represented by the general formula [9] [1 to 2 times in molar amount to the compound represented by the general formula [8]], and an acid anhydride represented by the general formula [10] [1 to 20 times in molar amount to the compound represented by the general formula [8]] (for example, acetic anhydride, propionic anhydride, butyric anhydride, benzoic anhydride, and the like) are dissolved in a solvent (carboxylic acid such as, for example, acetic acid, propionic acid, butyric acid; nitriles such as, for example, acetonitrile, propionitrile, n-butyronitrile) if necessary, and the solution is reacted at 0 to 150° C. (preferably 40 to 120° C.) for 0.1 to 24 hours (preferably 0.5 to 12 hours, and more preferably 1 to 8 hours), to obtain the compound represented by the general formula [11].

Subsequently, the compound represented by the general formula [11] and a compound represented by the general formula [12] (a pyrazole structurepart) [0.5 to 10 times, preferably 1 to 5 times in molar amount to the compound represented by the general formula [11]] are reacted in the presence of a basic catalyst (organic amines such as, for example, pyridine, triethylamine, N,N-dimethylaniline, piperidine, 4-dimethylaminopyridine, 1,5-diazabicyclo[4.3.0]non-5-ene, 1,8-diazabicyclo[5.4.0]undec-7-ene, tri-n-butylamine; metal hydrides such as, for example, sodium hydride; basic alkali metal compounds such as, for example, n-butyllithium), using a dehydration condensation agent [inorganic dehydration agents such as, for example, concentrated sulfuric acid, phosphorus pentoxide, anhydrous zinc chloride; carbodiimides such as, for example, dicyclohexylcarbodiimide, diisopropylcarbodiimide, 1-ethyl-3-(3-dimethylaminopropyl)carbodiimide) hydrochloride; acetic anhydride; polyphosphoric acid; carbonyldiimidazole; p-toluenesulfonyl chloride; and the like], and if necessary in a solvent (amides such as, for example, N,N-dimethylformamide (DMF), N,N-dimethylacetamide (DMA), acetamide, N-methylpyrolidone; nitriles such as, for example, acetonitrile, propionitrile, n-butyronitrile; alcohols such as, for example, methanol, ethanol, propanol, isopropanol, butanol, ethylene glycol, 1,4-butandiol; ethers such as, for example, tetrahydrofuran, dioxane, anisole, ethylene glycol monoethyl ether; sulfoxides such as, for example, dimethylsulfoxide) at 0 to 150° C. (preferably 40 to 120° C.) for 0.1 to 24 hours (preferably 0.5 to 12 hours, and more preferably 1 to 8 hours), to obtain the desired compound II' represented by the general formula [1'].

A method for introducing the group represented by the general formula [101] relevant to the present invention will be explained below by taking for example a case where a compound represented by the general formula [24] [that is, a compound corresponding to a case where $R^{1'}$ is an alkyl group having as a substituent a group represented by the general formula [101] in the general formula [1'] (a group corresponding to the case where $R^{104}$ is a hydrogen atom)], among the compounds represented by the general formula [1'], is synthesized:

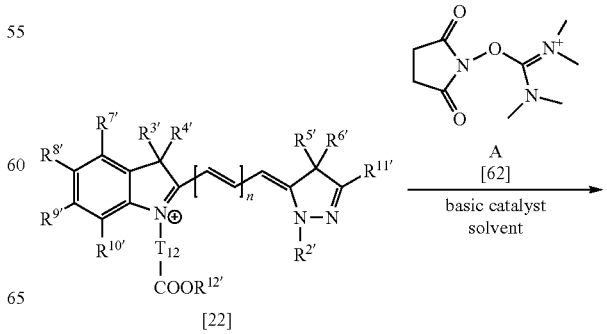

-continued

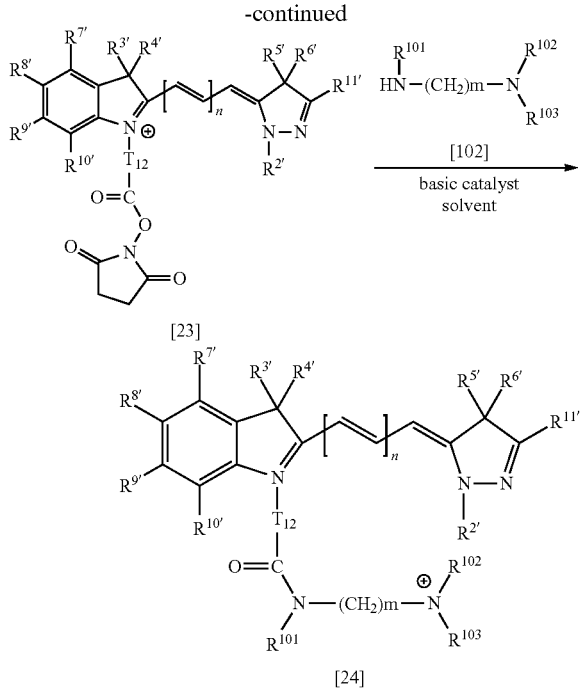

[23]

[24]

(wherein $T_{12}$ represents an alkylene group, A represents a tetrafluoroborate or a hexafluorophosphate, and $R^{3'}$ to $R^{11'}$, $R^{12'}$, $R^{101}$ to $R^{103}$, A, m and n are the same as above).

It should be noted that the compound represented by the general formula [22] corresponds to a compound where $R^{1'}$ is an alkyl group having, as a substituent, a group represented by the general formula [2] (that is, a group corresponding to -$T_{12}$-COOR$^{12}$ group), among the compounds represented by the general formula [1'].

In the general formulas [22] to [24], the alkylene group represented by $T_{12}$ may be any of straight-chained or branched one, and preferably straight-chained one of usually $C_1$ to $C_6$, and preferably $C_1$ to $C_4$. Specifically, the group includes a straight-chained alkylene group such as, for example, a methylene group, an ethylene group, a trimethylene group, a tetramethylene group, a pentamethylene group, a hexamethylene group; a branched alkylene group such as an ethylidene group, a propylidene group, an isopropylidene group, an ethylethylene group, a 1,2-dimethylethylene group, a 1,2-diethylethylene group, a 1,2-di-n-propylethylene group, a 1,2-di-n-butylethylene group; and the like, and among them, a straight-chained alkylene group is preferable, in particular, an ethylene group, a pentamethylene group and the like are more preferable.

That is, a compound represented by the general formula [22] is reacted with a succinimidization reagent such as, for example, a compound represented by the general formula [62] (1 to 10 times in molar amount to the compound represented by the general formula [22]) in the presence of a basic catalyst (organic amines such as, for example, N-ethyldiisopropylamine, pyridine, triethylamine, N,N-dimethylaniline, piperidine, 4-dimethylaminopyridine, 1,5-diazabicyclo [4.3.0]non-5-ene, 1,8-diazabicylo[5.4.0]undec-7-ene, tri-n-butylamine) in an appropriate solvent (amides such as, for example, DMF, DMA, acetamide, N-methylpyrolidone) at 0 to 40° C. for 0.1 to 12 hours, to obtain the compound represented by the general formula [23].

Subsequently, the compound represented by the general formula [23] is reacted with a cationization reagent, for example, represented by the general formula [102] (1 to 5 times in molar amount to the compound represented by the general formula [23]) in an appropriate solvent (amides such as, for example, DMF, DMA, acetamide, N-methylpyrolidone) at 0 to 40° C. for 0.1 to 12 hours, to obtain the compound represented by the general formula [24].

The succinimidation reagent relevant to the present invention includes not only the compound represented by the above-described general formula [62] but also all of those to be usually used in this field, and specifically includes, for example, di(N-succinimidyl)carbonate (DSC), 2-succinimide-1,1,3,3-tetramethyluronium tetrafluoroborate (TSTU), 2-(5-norbornene-2,3-dicarboxylmide)-1,1,3,3-tetramethyluronium tetrafluoroborate (TNTU), and the like. In addition, when succinimidation reaction is carried out, the reaction may be carried out in the presence of an appropriate basic catalyst (organic amines such as, for example, triethylamine, N-ethyldiisopropylamine, pyridine, N,N-dimethylaniline, piperidine, 4-dimethylaminopyridine, 1,5-diazabicyclo [4.3.0]non-5-ene, 1,8-diazabicylo[5.4.0]undec-7-ene, tri-n-butylamine).

A method for synthesizing the compound represented by the general formula [8] (an indolenine structure part) will be explained below:

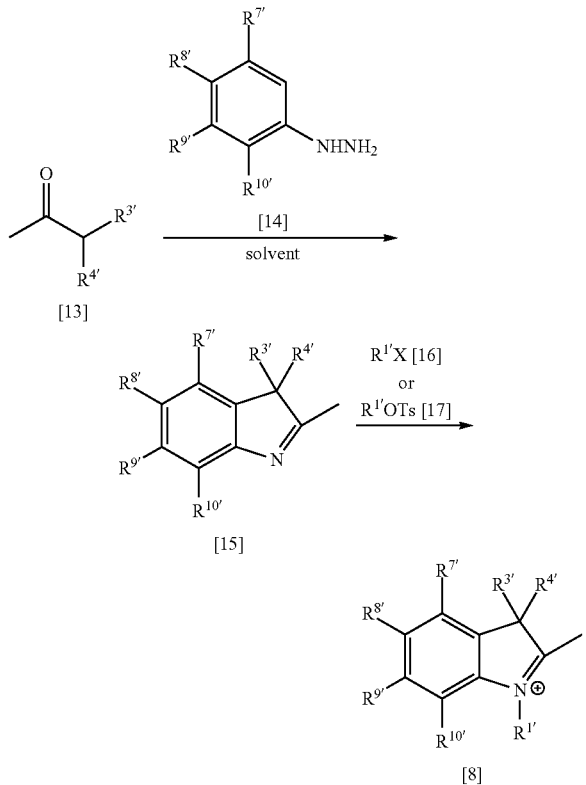

(wherein, X represents a halogen atom, $R^{1'}$, $R^{3'}$, $R^{4'}$ and $R^{7'}$ to $R^{10'}$ are the same as above).

In the general formula [16], the halogen atom represented by X includes, for example, a fluorine atom, a chlorine atom, a bromine atom, an iodine atom.

That is, a ketone compound represented by the general formula [13] and a compound represented by the general formula [14] are reacted in an appropriate solvent (carboxylic acids such as, for example, acetic acid, propionic acid; alcohols such as, for example, ethylene glycol, 1,4-butanediol) at 40 to 250° C. for 0.1 to 24 hours, to obtain a compound represented by the general formula [21] (see, for example, Journal of Organic Chemistry, 42(14), 2474-80, 1977, etc.).

Subsequently, a compound represented by the general formula [15] along with a halide represented by the general formula [16] or a tosylate compound represented by the general formula [17] are dissolved in an appropriate solvent (halogenated aromatic hydrocarbons such as, for example, chlorobenzene, 1,2-dichlorobenzene; halogenated hydrocarbons such as, for example, 1,2-dichloroethane; aromatic hydrocarbons such as, for example, toluene, xylene, benzene; amides such as, for example, DMF, DMA, acetamide, N-methylpyrolidone; and the like), and the mixture is reacted at 40 to 200° C. for 1 to 24 hours, to obtain a compound represented by the general formula [8] (see, for example, J. Chem. Soc., Perkin Trans. 1, 947-952, 1984, etc.).

The ketone compound represented by the general formula [13], may use a commercial product (for example, 3-methyl-2-butanone, 3-methyl-2-pentanone, 3-methyl-2-hexanone, 1-cyclopropylethanone, 1-cyclobutylethanone, and the like), or one synthesized as appropriate by a usual method. An example of synthesis of said ketone compound includes, for example, a method where ethyl 2-methylacetoacetate is reacted with a compound having a leaving group (for example, a halogen atom, a tosylate group, and the like) in the presence of a basic catalyst (metal hydrides such as, for example, sodium hydride, potassium hydride; alkali metal carbonate such as, for example, lithium carbonate, sodium carbonate, potassium carbonate; alkali metal alkoxides such as, for example, sodium methoxide, sodium ethoxide, potassium tert-butoxide; basic alkali metal compounds such as, for example, n-butyllithium; alkali metal amides such as, for example, lithium diisopropylamide) in an appropriate solvent (amides such as, for example, DMF, DMA, acetamide, N-methylpyrolidone; alcohols such as, for example, methanol, ethanol, propanol, isopropanol, butanol, ethylene glycol; ethers such as, for example, tetrahydrofuran, dioxane, ethylene glycol monoethyl ether; sulfoxides such as, for example, dimethylsulfoxide) at −80 to 100° C. for 0.1 to 24 hours, subsequently the resultant solution is subjected to decarboxylation using an acid catalyst (see, for example, Modern Synthetic Reactions, California, 2'nd ed., P. 492, 510 and 756 (1972), etc.), and the like.

The compound represented by the general formula [14] may use a commercial product, or one synthesized as appropriate by a usual method.

A method for synthesizing the compound represented by the general formula [12] (a pyrazole structure part) will be explained below:

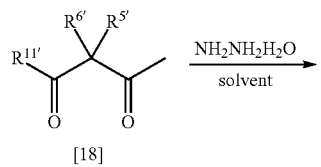

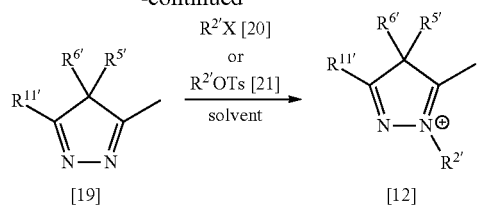

(wherein $R^2$, $R^{5'}$ to $R^{6'}$, $R^{11'}$ and X are the same as above).

That is, the diketone compound represented by the general formula [18] and hydrazine are subjected to dehydration reaction in an appropriate solvent (alcohols such as, for example, methanol, ethanol, propanol, isopropanol, butanol, ethylene glycol) at 60 to 100° C. for 1 to 4 hours, to obtain a 4H-pyrazole compound represented by the general formula [19] (see, for example, Adv. Heterocycle. Chem. Vol. 34, 53-78, 1983, etc.).

Subsequently, the 4H-pyrazole compound represented by the general formula [19], and a halide represented by the general formula [20] or a tosylate compound represented by the general formula [21] are subjected to N-alkylation reaction in an appropriate solvent (halogenated aromatic hydrocarbons such as, for example, chlorobenzene, 1,2-dichlorobenzene; halogenated hydrocarbons such as, for example, 1,2-dichloroethane; aromatic hydrocarbons such as, for example, toluene, xylene, benzene; amides such as, for example, DMF, DMA, acetamide, N-methylpyrolidone; and the like) at 80 to 140° C. for 1 to 12 hours, to obtain the compound represented by the general formula [12] (see, for example, J. Chem. Soc., Perkin Trans. 1, 947-952, 1984, etc.).

The diketone compound represented by the general formula [18] may use a commercial product (for example, 3,3-dimethyl-2,4-pentan-dione, and the like), or one synthesized as appropriate by a usual method. An example of the synthesis of said ketone compound includes, for example, a method where 3-methyl-2,4-pentanedione or ethyl 4-acetyl-5-oxohexanoate ester is reacted with a compound having a leaving group (for example, a halogen atom, a tosylate group, and the like) in the presence of a basic catalyst (metal hydrides such as, for example, sodium hydride, potassium hydride; alkali metal carbonates such as, for example, lithium carbonate, sodium carbonate, potassium carbonate; alkali metal alkoxides such as, for example, sodium methoxide, sodium ethoxide, potassium tert-butoxide; basic alkali metal compounds such as, for example, n-butyl lithium; alkali metal amides such as, for example, lithium diisopropylamide; and the like) in an appropriate solvent (amides such as, for example, DMF, DMA, acetamide, N-methylpyrolidone; alcohols such as, for example, methanol, ethanol, propanol, isopropanol, butanol, ethylene glycol; ethers such as, for example, tetrahydrofuran, dioxane, ethylene glycol monoethyl ether, and the like; sulfoxides such as, for example, dimethylsulfoxide; and the like) at −80 to 100° C. for 0.1 to 24 hours (see, for example, Modern Synthetic Reactions, California, 2'nd ed., p. 492, 510, 756 (1972), etc.), and the like.

[The Compound III Having 3 or More Cation Groups in a Molecule Relevant to the Present Invention (Hereinafter, Sometimes Abbreviated as the Cation-Group-Containing Compound III Relevant to the Present Invention)]

The cation-group-containing compound III relevant to the present invention is a compound having in a molecule usually 3 to 10 cation groups, preferably 5 to 8 cation groups, and more preferably 5 to 6 cation groups. Since the compound as described above has a faster migration velocity when it is electrophoretically migrated in a direction from plus side to minus side, a peak of the compound is detected in an ealier time than that of any analytes, and hence the compound can be used as a useful internal standard substance. The above-described cation group includes ammonium ion such as, for example, a dimethylammonium ion, a diethylammonium ion, a trimethylammonium ion, and the like; and the like.

[The Compound IV where 1 to 3 Groups of Cation Groups of the Cation-Group-Containing Compound III Relevant to the Present Invention have been Substituted by Anion Groups (Hereinafter, Sometimes Abbreviated as the Anion-Group-Introduced Compound IV Relevant to the Present Invention)]

The anion-group-introduced compound IV relevant to the present invention is a compound having the same skeleton as that of the cation-group-containing compound III relevant to the present invention where 1 to 3 groups of the cation groups have been substituted by anion groups. Due to this structure, when this compound IV is electrophoretically migrated in a direction from plus side to minus side, it becomes possible to delay a migration time of this compound IV than that of the cation-group-containing compound III relevant to the present invention. That is, by substituting 1 to 3 cation groups by anion groups depending on a migration time of the analyte, when the cation-group-containing compound III relevant to the present invention and the anion-group-introduced compound IV relevant to the present invention are used in combination as internal standard substances, it becomes possible that a peak of the analyte is allowed to be positioned between peaks of the two internal standard substances.

[Measurement Method of the Present Invention]

The measurement method of the present invention is a method where (1) a combination of the anion-group-containing compound I and the cation-group-containing compound II both relevant to the present invention and (2) a combination of the cation-group-containing compound III and the anion-group-introduced compound IV both relevant to the present invention are used as internal standard substances as described above (hereinafter, sometimes the combinations of the above-described compounds are collectively abbreviated as internal standard substance relevant to the present invention), and preferably a combination of the anion-group-containing compound I relevant to the present invention and the cation-group-introduced compound II relevant to the present invention is used. It should be noted that when the above-described combinations are used as internal standard substances, one or more kinds of internal standard substances may be further added to the above-described combinations. That is, for example, a combination of one kind of the anion-group-containing compound I relevant to the present invention and two kinds of the cation-group-introduced compound II relevant to the present invention, a combination of two kinds of the anion-group-containing compound I relevant to the present invention and one kind of the cation-group-introduced compound II relevant to the present invention, a combination of two kinds of the cation-group-containing compound III relevant to the present invention and one kind of the anion-group-introduced compound IV relevant to the present invention, a combination of one kind of the cation-group-containing compound III relevant to the present invention and two kinds of the anion-group-introduced compound IV relevant to the present invention, or the like may be used as internal standard substances.

The analyte relevant to the measurement method of the present invention is not particularly limited but includes all substances being measured in this field. Specifically, the analyte includes, for example, peptide chain (for example, C-peptide, angiotensin I, and the like), protein [serum protein such as, for example, immunoglobulin A (IgA), immunoglobulin E (IgE), immunoglobulin G (IgG), immunoglobulin M (IgM), immunoglobulin D (IgD), β2-microglobulin, albumin, degradation product thereof, ferritin; enzyme protein such as, for example, amylase, alkaline phosphatase, γ-glutamyltransferase; protein, peptide or sugar chain derived from bacterium such as, for example, tuberculosis bacterium, pneumococcus, *diphtheria bacillus, meningococcus, gonococcus, staphylococcus, streptococcus*, intestinal bacterium, coli bacterium, *Helicobacter pylori*; virus such as, for example, rubella virus, herpes virus, hepatitis virus, ATL virus, AIDS virus, influenza virus, adenovirus, enterovirus, poliovirus, EB virus, HAV, HBV, HCV, HIV, HTLV; fungus such as, for example, *candida, cryptococcus; spirochete* such as *leptospira, pallidum Treponema*; microorganisms such as chlamydia, mycoplasma; various kinds of allergens causing allergy such as bronchial asthma, allergic rhinitis, atopic dermatitis such as allergens derived from, for example, house dust; mites such as, for example, *dermatophagoides* and farina, *dermatophagoides pteronyssinus*; pollen of, for example, Japanese cedar, Japanese cypress, Paspalum thunbergii Kunth, blackweed, timothy grass, vernal grass, rye; animals such as, for example, cat, dog, crab; foods such as, for example, rice, egg white; fungus, insect, wood, medical agent, chemical substance, and the like; lipid such as, for example, lipoprotein; protease such as, for example, trypsin, plasmin, serine protease; tumor marker protein such as, for example, AFP, PSA, CEA, PG I, PG II; and the like], sugar chain (tumor marker sugar chain antigen sugar chain such as, for example, CA 19-9, PIVKA-II, CA 125, sugar chain possessed by a substance having a particular sugar chain produced by cancer cell; for example, ABO sugar chain, and the like), lectin (for example, concanavalin A, lentils lectin, marrow bean lectin, angel trumpet lectin, wheat germ lectin, and the like), phospholipid (for example, cardiolipin, and the like), lipopolysaccharide (for example, endotoxin, and the like), chemical substance (hormone such as, for example, PTH, T3, T4, TSH, insulin, LH, FSH, prolactin; endocrine disrupters such as, for example, tributyltin, nonylphenol, 4-octylphenol, di-n-butyl phthalate, dicyclohexyl phthalate, benzophenone, octachlorostyrene, di-2-ethylhexyl phthalate), receptor (for example, receptor for estrogen, TSH, and the like), ligand (for example, estrogen, TSH, and the like), and among them, tumor marker protein such as, for example, AFP, PSA, CEA, PG I, PG II, and tumor marker sugar chain antigen sugar chain such as, for example, CA 19-9, PIVKA-II, CA 125, sugar chain possessed by a substance having a particular sugar chain produced by cancer cell, are preferable, and AFP and PIVKA-II are particularly preferable.

The capillary electrophoresis method relevant to the present invention includes all of the methods usually used in this field, and among them, an electrophoresis method carried out in a capillary chip is preferable. The capillary (micro) chip electrophoresis method is a technology where a capillary having a cross-section of 100 μm or less in diameter is formed on a substrate of a chip and electrophoresis is carried out in the capillary, and a method by which substances present in a sample are separated utilizing a difference in charge as a difference in mobility by applying electric voltage to inside of the capillary.

The capillary electrophoresis method can be classified into capillary zone electrophoresis method and capillary gel electrophoresis method depending on a migration solution to be used, and the method of the present invention can be applied to both of them. Among the above methods, capillary gel electrophoresis method is preferable in view of accuracy of separation.

Material of the capillary to be used for the above-described capillary electrophoresis method is not particularly limited, and any material commonly used in this field may be used. Specifically, the material includes, for example, silica-based compound such as, for example, glass, quartz, silicon; synthetic polymer such as, for example, cyclic olefin copolymer (COC), cyclic olefin polymer (COP), polymethyl methacrylate, polymethyl siloxane, polyvinyl chloride, polyurethane, polystyrene, polysulfon, polycarbonate, polytetrafluoroethylene; and the like, and among them, synthetic polymer is preferable. In addition, internal diameter and length of the capillary are not particularly limited so long as an analyte can be separated, but internal diameter is usually 1 to 1000 μm, preferably 1 to 200 μm, and more preferably 1 to 100 μm. Length is usually 0.1 mm to 100 cm, preferably 0.1 mm to 20 cm, and more preferably 0.1 mm to 10 cm.

Migration solution to be used in the capillary electrophoresis method relevant to the present invention is not particularly limited, and any solution commonly to be used in this field may be used. In the case of the capillary zone electrophoresis method, specifically the migration solution includes, for example, a buffer solution of pH 5 to 10, preferably pH 6 to 8, and the buffer solution can specifically include but not limited to, for example, a lactate buffer, a citrate buffer, an acetate buffer, a succinate buffer, a glycine buffer solution, a phthalate buffer, a phosphate buffer, a triethanolamine buffer, a barbiturate buffer, a tris(hydroxymethyl)aminomethane-hydrochloride buffer solution, a tartrate buffer solution, a borate buffer solution, and the like. In addition, in the case of the capillary gel electrophoresis method, the migration solution includes the one where a polymer, for example, polyether such as, for example, polyethylene oxide (polyethylene glycol), polypropylene oxide; polyalkyleneimine such as, for example, polyethyleneimine; polyacrylic acid-based polymer such as, for example, polyacrylic acid, polyacrylate ester, polymethyl methacrylate; polyamide-based polymer such as, for example, polyacrylamide, polymethacrylamide; polymethacrylic acid-based polymer such as, for example, polymethacrylic acid, polymethacrylate ester, polymethyl methacrylate; polyvinyl-based polymer such as, for example, polyvinyl acetate, polyvinyl pyrolidone, polyvinyl oxazolidone; water-soluble hydroxyl polymer such as, for example, pullulan, elusinan, xanthan, dextran, guagum; water-soluble cellulose compound such as, for example, methylcellulose, hydroxyethylcellulose, hydroxypropylcellulose, and the like; derivatives thereof; copolymers containing plural kinds of monomer units constituting these polymers; and the like is added to the buffer solutions to be used as a migration solution for the above-described capillary zone electrophoresis. It should be noted that the above-described polymers may be added in a combination of two or more kinds. In addition, molecular weight of the above-described polymers as mentioned above is usually 500 Da to 6000 kDa, preferably 1 to 1000 kDa, and more preferably 100 to 1000 kDa. In addition, concentration of the above-described polymers may be appropriately selected from a range usually used in this field, and is usually 0.01 to 40% (W/V), preferably 0.01 to 20% (W/V), and more preferably 0.1 to 10% (W/V). It should be noted that viscosity of the buffer solution for migration when the above-described filler is added to the buffer solution for migration is usually 1 to 50 centipoise, preferably 1 to 20 centipoise, and more preferably 1 to 10 centipoise.

The above-described migration solution may contain a substance to reduce an effect of electroosmotic flow such as, for example, polyacrylamide, polyethylene glycol, polyethyleneimine, fluorine-containing aromatic hydrocarbon, sugars, and the like, and concentration thereof may be set in a range usually to be used in this field.

Since voltage at migration in the capillary electrophoresis method relevant to the present invention varies depending on migration solution, equipment to be used, or the like, the voltage may be appropriately set in a range to be usually used in this field.

Method for introducing a sample in the capillary electrophoresis method relevant to the present invention or an internal standard substance relevant to the present invention is not particularly limited, and may be a method usually used in this field. The method includes, for example, aspiration method, pressurization method, electric introduction method, and the like. Among them, pressurization method is preferable. It should be noted that the internal standard substance relevant to the present invention may be introduced by either method where the internal standard substance is dissolved in a sample in advance or a method where a sample and a solution containing the internal standard substance are introduced separately. Amount of the internal standard substance to be introduced varies depending on conditions such as internal diameter and length of capillary, type and sensitivity of detector, but usually the same amount as that of a sample to be introduced is used. Usually 0.001 to 100 fmol is introduced into the capillary. It should be noted that introduction of above-described sample or the internal standard substance relevant to the present invention may be carried out by concentrating by a known isotachophoresis (ITP) and thereafter introducing the concentrate to the capillary electrophoresis as it is. In this case, for example, when microchip electrophoresis is used, it is desirable to carry out the ITP electrophoresis and the capillary electrophoresis continuously using a chip where the ITP electrophoresis and the capillary electrophoresis are connected each other.

The sample to be used in the above-described capillary electrophoresis method is not particularly limited, and may be a solution containing the above-described an analyte. Specifically, the sample may be a solution containing the above-described an analyte. Specifically, the sample includes, for example, body fluid such as serum, plasma, spinal fluid, joint fluid, lymph fluid; excrement such as urine and faces; sample derived from living organism such as sputum, pus, substance derived from skin; environmental sample such as, for example, food, beverage, tap water, sea water, lake water, river water, factory effluent, washing water for semiconductor, cleaning water after cleansing medical devices, and the like; and processed liquid obtained by reconstituting by appropriately dissolving these substances in water, a buffer solution usually to be used in this field such as, for example, a Tris buffer, a phosphate buffer, a veronal buffer, a borate buffer, a Good's buffer; and the like.

The capillary electrophoresis method in the measurement method of the present invention is performed by filling the above-described migration solution into the above-described capillary, thereafter introducing the above-described sample and the internal standard substances, relevant to the present invention into the capillary by the above-described introducing method, carrying out an electrophoresis by applying a voltage usually used in this field, and measuring by detectors such as fluorescence detector, UV detector, or the like. More specifically, the method is performed by filling, for example, a Tris-HCl buffer containing 0.1 to 1.0% of polydimethylacrylamide, 1 to 5% glycerol, and 0.01 to 0.1% BSA into a capillary, for example, having an internal diameter of 50 to 100 μm and a length of 1 to 10 cm, introducing a sample containing one kind of internal standard substance into a capillary from the starting end thereof by the pressurization method at 1 to 10 psi for 30 to 60 seconds, subsequently introducing other internal standard substance into a capillary by the pressurization method at 1 to 10 psi for 30 to 60 seconds, after that carrying out an electrophoresis by applying, for example, a voltage of 1000 to 3000 V for 10 to 60 minutes, and measuring by a fluorescence detector.

In the measurement method of the present invention, the capillary electrophoresis is performed by carrying out an electrophoresis under such conditions as mentioned above, and measuring migration states of an analyte and the internal standard substances using a detector such as fluorescence detector, UV detector, to obtain an electropherogram, identifying peaks of the internal standard substances in said electropherogram, after that identifying a peak of an analyte from a migration time thereof, and the like.

More specifically, for example, when an analyte in a sample is measured using two internal standard substances, electrophoresis for the internal, standard substances and a standard substance of the analyte is carried out in advance, and migration times of two internal standard substances and the analyte, ratio of migration times between respective internal standard samples, and ratios of migration times between the internal standard substances and the analyte are measured. Subsequently, electrophoresis of the sample and the analyte is carried out under the same conditions, and peaks of two internal standard substances are identified from their migration times and the ratios of migration times between respective internal standard substances obtained in advance. Finally, peak of the analyte is identified from migration times of said two internal standard substances and ratios of migration times between respective internal standard substances and the analyte obtained in advance.

Hereinafter, Experimental Examples and Examples of the present invention will be described, however, the present invention is not limited thereto.

EXAMPLES

Experimental Example 1

Synthesis of Internal Standard Substance Relevant to the Present Invention 1

The following internal standard substance relevant to the present invention 1 was synthesized.

(1) Firstly, indolenine compound 8 was synthesized as follows.

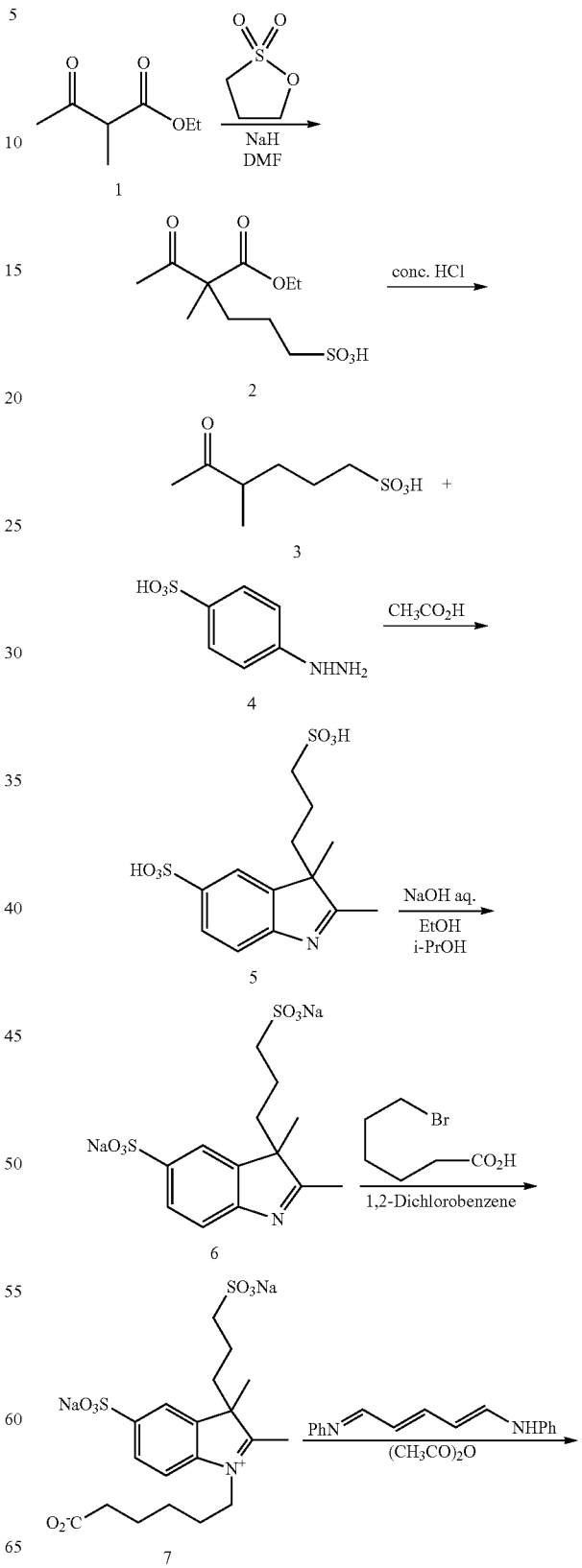

-continued

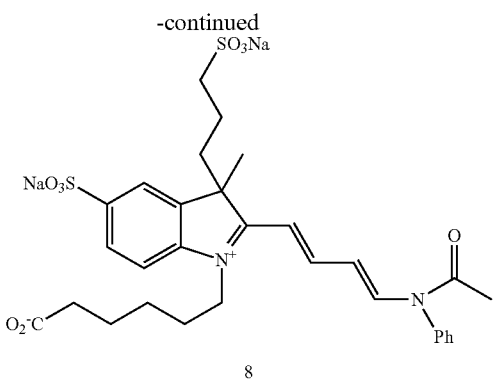

* Et = ethyl group, Ph = phenyl group

Details are explained below.

[Synthesis of Compound 2]

Ethyl-2-methylacetoacetate (1) (25.0 g, 0.173 mol), 1,3-propanesultone (23.3 g, 0.190 mol) and sodium hydride (8.5 g, 0.208 mol) were added to N,N-dimethylformamide (DMF) (80 ml), and the solution was reacted with stirring at 90° C. overnight. After completion of the reaction, the solvent was distilled off under reduced pressure, and the residual mixture was washed twice by adding water (200 ml) and diethyl ether (200 ml). After that, the aqueous layer part was distilled off under reduced pressure to obtain compound 2 (42.1 g, yield: 91%).

[Synthesis of Compound 3]

Compound 2 (40.5 g, 0.152 mol) was reacted in concentrated hydrochloric acid (60 ml) with stirring at 100° C. for 3 hours. After completion of the reaction, the solvent was distilled off under reduced pressure, and the product was purified by using silica gel column chromatography (eluate:methanol) to obtain compound 3 (16.6 g, yield: 56%).

[Synthesis of Compound 5]

Compound 3 (10.0 g, 0.051 mol) and compound 4 (12.9 g, 0.066 mol) in acetic acid (50 ml) were heated under reflux at 120° C. for 4 hours. After completion of the reaction, the solvent was distilled off under reduced pressure, and the product was purified by using reverse phase column chromatography (eluate:water) to obtain compound 5 (11.5 g, yield: 65%).

Property data: IR (KBr) (cm$^{-1}$): 3450, 1196

[Synthesis of Compound 6]

Compound 5 (11.5 g, 0.033 mol) was dissolved in water (50 ml) and ethanol (50 ml), and the solution was reacted with stirring at room temperature for 4 hours. After completion of the reaction, the solvents were distilled off under reduced pressure, and the product was purified by using reverse phase column chromatography (eluate:water) to obtain compound 6 (10.3 g, yield: 80%).

Property data: Mass (nega=346)
IR(KBr) (cm$^{-1}$): 3444, 1193

[Synthesis of Compound 7]

Compound 6 (10.0 g, 0.026 mol) and 6-bromohexanoic acid (9.97 g, 0.052 mol) were dissolved in 1,2-dichlorobenzene (100 ml), and the solution was reacted with stirring at 120° C. overnight. After completion of the reaction, the solvent was distilled off under reduced pressure, and the residual mixture was washed with ethyl acetate 3 times to obtain compound 7 (11.5 g, yield: 89%).

Property data: Mass (nega=460)
IR (KBr) (cm$^{-1}$): 3446, 1723, 1194

[Synthesis of Compound 8]

Compound 7 (1.5 g, 2.967 mmol) and malonaldehydeanilide hydrochloride (0.77 g, 2.967 mmol) were dissolved in acetic anhydride (20 ml), and the solution was reacted with stirring at 120° C. for 1 hour. After completion of the reaction, the solvent was distilled off under reduced pressure, and the product was purified by using reverse phase column chromatography (eluate: 10% aqueous solution of acetonitrile to obtain indolenine compound 8 (0.18 g, yield: 10%).

Property data: Mass (nega:posi=631:633)
IR (KBr) (cm$^{-1}$): 3443, 1716, 1574, 1465, 1189

(2) Synthesis of Pyrazole Compound 12

Subsequently, pyrazole compound 12 was synthesized as described below.

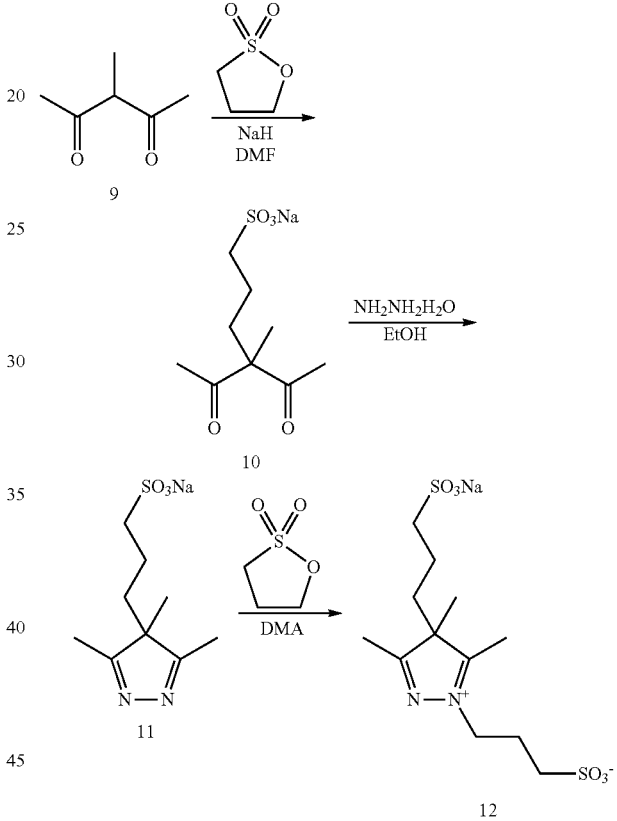

*DMA = dimethylacetamide

Details are explained below.

[Synthesis of Compound 10]

In DMF (100 ml), 3-methyl-2,4-pentandione (compound 9) (15.0 g, 0.13 mol), 1,3-propanesultone (16.1 g, 0.13 mol) and sodium hydride (5.0 g, 0.208 mol) was reacted with stirring at 50° C. for 16 hours. After completion of the reaction, the solution was neutralized with 1N sodium hydroxide, the solvent was distilled off under reduced pressure, and the residual mixture was washed twice by adding water (200 ml) and diethyl ether (200 ml). After that, the aqueous layer part was distilled off under reduced pressure to obtain pyrazole compound 10 (32.2 g, yield: 96%).

Property data: IR (KBr) (cm$^{-1}$): 3474, 1695, 1665, 1191

[Synthesis of Compound 11]

Compound 10 (10.0 g, 0.042 mol) and hydrazine monohydrate (2.1 g, 0.042 mol) were dissolved in ethanol (150 ml), and the solution was reacted with stirring at 80° C. for 3 hours.

After completion of the reaction, the solvent was distilled off under reduced pressure, and the product was purified by using silica gel column chromatography (eluate:methanol/chloroform=1/1) to obtain compound 11 (9.0 g, yield: 92%).

Property data: IR (KBr) 3421, 1195

[Synthesis of Compound 12]

Compound 11 (4.8 g, 0.019 mol) and 1,3-propanesultone (2.5 g, 0.02 mol) were dissolved in dimethylacetamide (30 ml), and the solution was stirred at 140° C. for 4 hours. After completion of the reaction, ethyl acetate (200 ml) was added to deposit a crystal, which was filtered to give the pyrazole compound (12) (5.3 g, yield: 76%).

Property data: Mass (nega=352)

IR (KBr) (cm$^{-1}$): 3446, 1194

(3) Syntheses of Indolenine Compound—Pyrazole Compound Complex 13

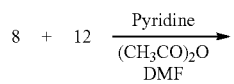

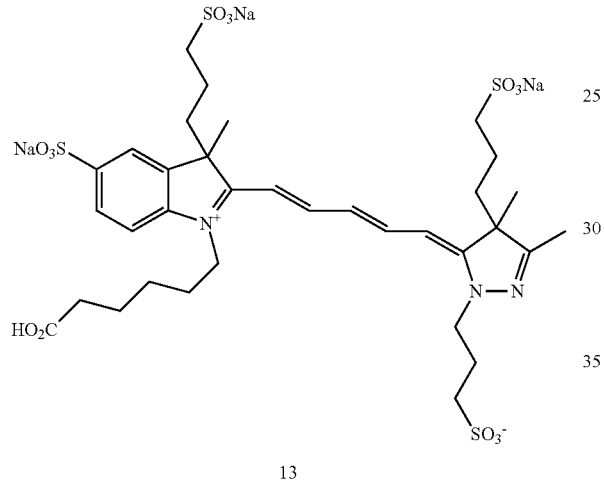

13

Indolenine compound 8 (0.1 g, 0.158 mmol) obtained in Example 1-(1) and pyrazole compound 12 (0.17 g, 0.474 mmol) obtained in Example 1-(2) were dissolved in DMF (2 ml), and pyridine (1 ml) and acetic anhydride (0.5 ml) were further added thereto. The solution was stirred at 80° C. for 1 hour. After completion of the reaction, the solvent was distilled off under reduced pressure, and the product was purified by using reverse phase column chromatography (eluate: 10% aqueous methanol solution) and Sephadex LH-20 [ manufactured by GE Healthcare Bioscience Co., Ltd. (former name: Amersham Bioscience Co. Ltd.)] (eluate:methanol) to obtain compound 13 (15 mg, yield: 12%). In the following Examples, said compound 8 was used as the internal standard substance.

Property data: Mass (nega=850)

Fluorescence characteristics of compound 13 are shown below.

TABLE 1

| Maximum absorption wavelength (λmax) | 634 nm |
| Molar absorption coefficient (ε) | 230,000 M$^{-1}$cm$^{-1}$ |
| Maximum excitation wavelength [Ex(max)] | 635 nm |
| Maximum fluorescence wavelength [Em(max)] | 655 nm |

Experimental Example 2

Synthesis Method for the Cation-Group-Introduced Internal Standard Substance

The following compound was synthesized according to the following synthetic reaction. It should be noted that said compound 15 was used as internal standard substance 2 in the following Example.

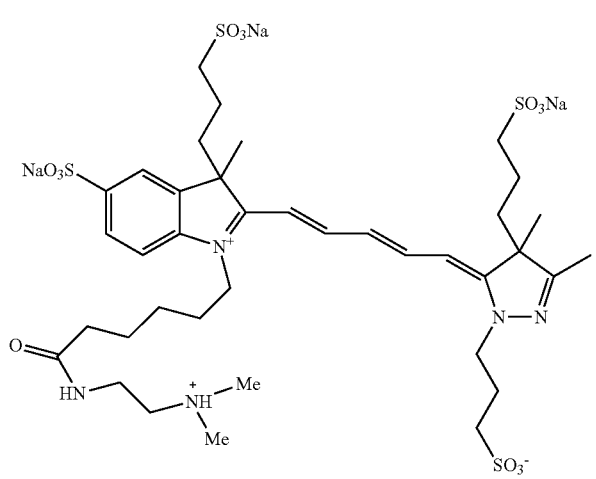

15

*Me = methyl group

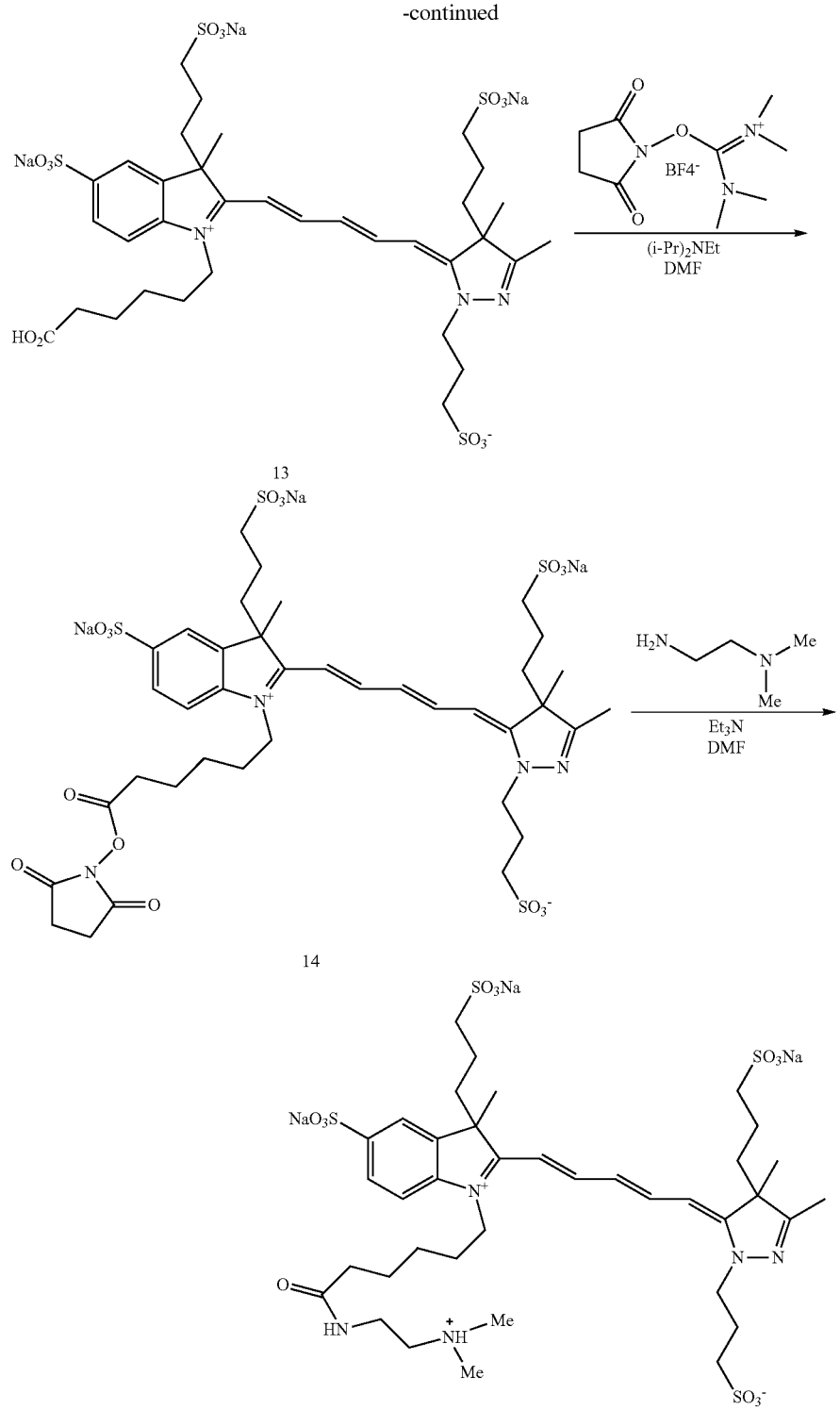

(1) Synthesis of Indolenine Compound—Pyrazole Compound Complex 14

Compound 13 (13 mg, 0.015 mmol) obtained by (1) in Example 1 was dissolved in DMF (0.6 ml), and 2-succinimide-1,1,3,3-tetramethyluronium tetrafluoroborate (TSTU) (46 mg) and N-ethyldiisopropylamine [(i-Pr)$_2$NEt] (600 μl) were added thereto. The solution was stirred at room temperature for 1 hour. After completion of the reaction, the product was crystallized by adding ethyl acetate (15 ml) and centrifuged to obtain compound 14 (13 mg, yield: 90%).

Property data: Mass (nega=947)

(2) Synthesis of Indolenine Compound—Pyrazole Compound Complex 15

The above-described compound 14 (7 mg) was dissolved in DMF (0.5 ml), and N,N-dimethylaminoethylamine (10 mg) and triethylamine (Et$_3$N) (2 μl) were added thereto. The solution was stirred for 3 hours. After completion of the reaction, the solvent was distilled off under reduced pressure, and the product was purified by using preparative reverse phase column to obtain compound 15 (3.2 mg). It should be noted that said compound 15 was used as internal standard substance 2 in the following Examples.

Property data: Mass (nega=933)

Fluorescence characteristics of compound 15 are shown below.

TABLE 2

| Maximum absorption wavelength (λmax) | 634 nm |
| Molar absorption coefficient (ε) | 230,000 $M^{-1}cm^{-1}$ |
| Maximum excitation wavelength [Ex(max)] | 635 nm |
| Maximum fluorescence wavelength [Em(max)] | 655 nm |

Example 1

Separation and Measurement of AFP

[Analyte (Antigen)]

α-fetoprotein (AFP) (manufactured by Wako Pure Chemical Industries, Ltd.)

[Mobility Change Binding Substance (DNA-Labeled Antibody)]

According to the procedure shown in FIG. 1, a DNA-bound anti-AFP antibody Fab' fragment was prepared.

That is, firstly, a 250 bp DNA fragment introduced with $NH_2$ group in 5' terminal was purified by a common method (purified terminally-aminated DNA), subsequently the NNS group introduced in this DNA fragment was reacted with a succinimide group of sulfosuccinimidyl 4-(p-maleimidephenyl)butylate (Sulfo-SMPB) linker (a linker having a succinimide group and a maleimide group, manufactured by Pierce Biotechnology, Inc.) by a common method, and then unreacted linker was removed by subjecting to gel filtration treatment, to obtain a linker-bound 250 bp DNA fragment. The obtained linker-bound 250 bp DNA fragment was reacted with anti-AFP antibody WA1 Fab' fragment prepared by using anti-AFP antibody WA1 (manufactured by Wako Pure Chemical Industries, Ltd.) according to a common method in advance. The obtained product was purified using DEAE column to prepare an anti-AFP antibody WA1 Fab' fragment to which a 250 bp DNA fragment was bound (250 bp DNA-labeled antibody).

[Labeled Binding Substance (Fluorescence-Labeled Antibody)]

Anti AFP antibody WA2 (manufactured by Wako Pure Chemical Industries, Ltd.) which recognizes epitope of AFP different from WA1 antibody was treated by a common method to prepare an anti-AFP antibody WA2 Fab' fragment, and then a fluorescent substance HyLyte 647 (manufactured by AnaSpec, Inc.) was introduced into an amino group of said fragment by a common method, to prepare a HyLyte 647-labeled anti-AFP abtibody WA 2 Fab' fragment (fluorescence-labeled antibody).

[Internal Standard Substance]

Internal standard substances 1 and 2 obtained, in Experimental Examples 1 and 2, respectively, were used.

[Capillary Chip]

A capillary chip having a layout shown in FIG. 2 was prepared as described below according to the method described in Technology and applications of micro chemical chip, Takehiko Kitamori, et al., 2004 ed. (Maruzen Co., Ltd.).

That is, a photoresist film was made on a Si deposited on a quartz substrate. Exposure was given to this photoresist using a mask having the capillary design (layout) illustrated in FIG. 2, and then development was carried out. Si in the part where photoresist was removed by the development was removed by sputtering, after that, wet etching was carried out using hydrogen fluoride solution to make a capillary channel grooves (capillary) on the quartz substrate. After removing photoresist and Si films remained on the quartz substrate, said quartz substrate and a cover plate having holes (wells) as liquid reservoirs were laminated by HF connection method to make a capillary chip.

Figure 2:
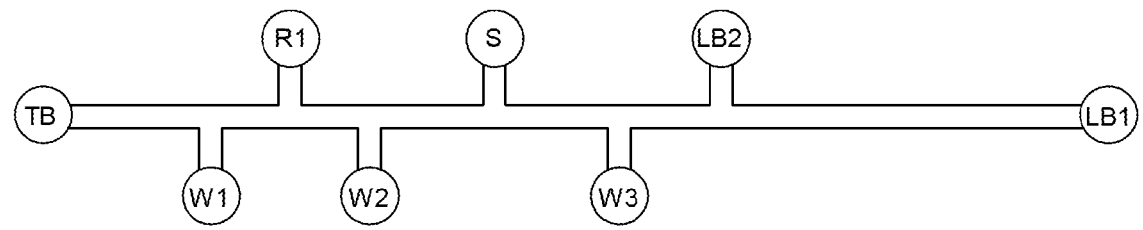
FIG. 2 is a drawing showing a layout of the capillary chip in Example 1.

It should be noted that, in FIG. 2, TB represents a well for introducing trailing buffer, LB1 and LB2 represent wells for introducing leading buffer, S represents a well for introducing migration sample, R1 represents a well for introducing test solution (250 bp DNA-labeled antibody-containing solution), W1, W2 and W3 represent wells for drain, respectively.

[Electrophoresis]

(1) Leading Buffer

A 75 mM Tris-HCl buffer (pH 7.5) containing 0.6% (w/v) of polydimethylacrylamide (pDMA), 3% (w/v) of glycerol, 75 mM of NaCl, 0.01% of bovine serum albumin (BSA) and 4 mg/ml of LCA was used as a leading buffer.

(2) Trailing Buffer

A 75 mM Tris buffer containing 0.6% (w/v) of pDMA, 3% (w/v) of glycerol, 0.01% of BSA and 125 mM of HEPES was used as a trailing buffer.

(3) Sample for Migration

A 75 mM Tris-HCl buffer (pH 7.5) containing 0.6% (w/v) of polydimethylacrylamide (pDMA), 3% (w/v) of glycerol, 75 mM of NaCl, 0.01% of BSA and 3.6 mM of MES was used as a sample buffer, and 1 μL of serum containing 100 μM of AFP, 1 μL of fluorescence-labeled antibody and 1 nM of internal standard substance 1 and 8 μL of the sample buffer were mixed in a 0.5 mL tube, to prepare 10 μL of reaction liquid.

The reaction liquid was placed on ice to allow an antigen-antibody reaction to progress for about 30 minutes, to form a fluorescence-labeled antibody-AFP immune complex. It should be noted that final concentration of the fluorescence-labeled antibody was 100 nM.

The obtained immune complex-containing reaction liquid was used as a sample for migration.

(4) Test Solution (250 bp DNA-Labeled Antibody-Containing Solution)

A leading buffer containing 100 nM of 250 bp DNA-labeled antibody and 1 nM of internal standard substance 2 (containing 50 mM of $Cl^-$ ion) was used as a test solution.

Figure 3:
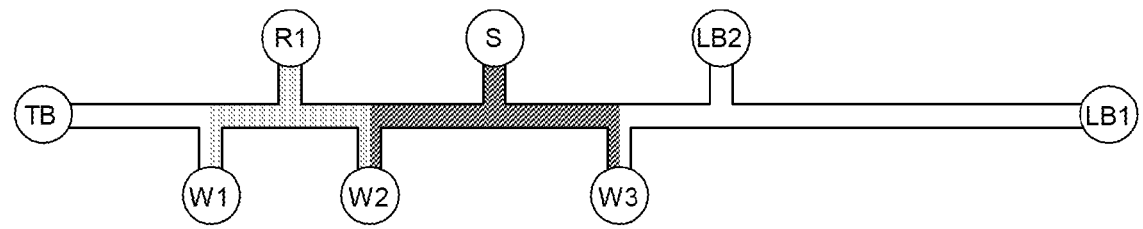
FIG. 3 is a drawing schematically showing arrangement of a sample for migration and a test solution in the capillary chip in Example 1.

(5) Procedures of Electrophoresis a) Introduction of the Sample for Migration and the Test Solution In FIG. 2, 10 μL of the sample for migration (fluorescence-labeled antibody-AFP immune complex-containing solution) to S well (a well for introducing a sample for migration), 10 μL of the test solution (DNA-labeled antibody-containing solution) to R1 well (a well for introducing a test solution), 10 μL of the leading buffer to LB1 well and LB2 well, and 10 μL of the trailing buffer to TB well were added dropwise, respectively. The sample for migration, the test solution, the leading buffer and the trailing buffer were introduced into channels by applying a pressure of −5 psi among W1 (a well for drain)-W2 (a well for drain)-W3 (a well for drain) for 30 seconds. Arrangement of the sample for migration and the test solution in a capillary is schematically shown in FIG. 3. It should be noted that in FIG. 3, the shaded part represents a part occupied by the sample for migration, and the point part represents a part occupied by the test solution.

b) ITP (Reaction, Concentration, Separation) Detection

By applying a voltage of 3000 V between TB well and LB1 well in FIG. 3, the 250 bp DNA-labeled antibody in the test solution was contacted with fluorescence-labeled antibody—AFP immune complex in the sample for migration at 30° C., to form an immune complex of fluorescence-labeled antibody—AFP—250 bp DNA-labeled antibody, which was then concentrated by isotachophoresis (ITP).

It should be noted that reaction time was about 100 seconds (as a time for 250 bp DNA-labeled antibody to pass through the zone of the sample for migration (the shaded zone). After the immune complex was migrated to LB2 and its passing through LB2 was judged from a change in voltage, negative electrode was switched from TB to LB2, and the capillary gel electrophoresis (CGE) was further carried out until a peak of the fluorescence-labeled antibody—AFP—250 bp DNA-labeled antibody immune complex was detected in the detection part (a capillary part 2 cm apart from the LB2 channel crossing part).

It should be further noted that detection was carried out over time by measuring an intensity of fluorescence generated by 635 nm laser excitation in the capillary part-2 cm apart from the LB2 channel crossing part, using a fluorescence microscope (BX-50, manufactured by KS Olympus Co., Ltd.).

[Results]

Figure 4:
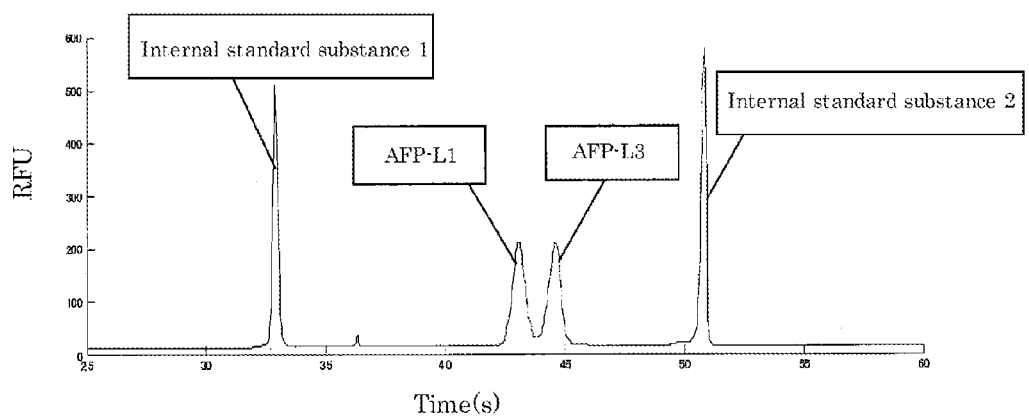
FIG. 4 is an electropherogram when AFP was measured by the method of the present invention in Example 1.

An electrophoretic profile (electropherogram) when the sample for migration was used is shown in FIG. 4. It should be noted that, in FIG. 4, the vertical axis represents fluorescence intensity, and the horizontal axis represents retention time, respectively.

From the results in FIG. 4, it was found that by carrying out electrophoresis using internal standard substances 1 and 2 relevant to the present invention as mentioned above, peaks of AFP-L1 and AFP-L3 to be measured were allowed to locate between both peaks of the internal standard substances, and thereby both peaks could be identified easily.

Example 2

Separation and measurement of PIVK II

[Analyte (Antigen)]

PIVK II was prepared according to the method described in Poser J W, Price P A, J. Biol. Chem. 1979, January 25; 254(2): 431-6.

[Mobility Change Binding Substance (DNA-Labeled Antibody)]

Preparation of the substance was carried out in the same way as in Example 1 except that PIVKA II Fab' fragment was used instead of anti-AFP antibody WA1 Fab' fragment, to obtain an anti-PIVKA II antibody Fab' fragment (250 bp DNA-labeled antibody).

[Labeled Binding Substance (Fluorescence-Labeled Antibody)]

An anti-prothrombin antibody prepared by a common method was treated to make an anti-prothrombin antibody Fab' fragment, and by introducing a fluorescent substance HiLyte 647 (manufactured by AnaSpec, Inc.) by a common method to an amino group of said fragment, HiLyte 647-labeled anti-prothrombin antibody Fab' fragment (fluorescence-labeled antibody) was prepared.

[Internal Standard Substance]

Internal standard substances 1 and 2 obtained in Experimental Examples 1 and 2, respectively, were used.

[Capillary Chip]

The same one as in Example 1 was used.

[Electrophoresis]

(1) Leading Buffer

The same one as in Example 1 was used.

(2) Trailing Buffer

The same one as in Example 1 was used.

(3) Sample for Migration

A 75 mM Tris-HCl buffer (pH 7.5) containing 0.6% (w/v) of polydimethylacrylamide (pDMA), 3% (w/v) of glycerol, 75 mM of NaCl, 0.01% of BSA and 3.6 mM of MES was used as a sample buffer, and 1 μL of serum containing 100 μM of PIVKA II, 1 μM of fluorescence-labeled antibody and 5 μL of 1.4 nM of internal standard substance 1 and 8 μL of the sample buffer were mixed in a 0.5 mL tube, to prepare a reaction liquid.

The reaction liquid was placed on ice to allow an antigen—antibody reaction to progress for about 30 minutes, to form a fluorescence-labeled antibody—PIVKA II immune complex. It should be noted that final concentration of the fluorescence-labeled antibody was 100 nM.

The obtained immune complex-containing reaction liquid was used as a sample for migration.

(4) Test Solution (250 bp DNA-Labeled Antibody-Containing Solution)

A leading buffer containing 200 nM 250 bp DNA-labeled antibody and 140 μM internal standard substance 2 (containing 50 mM Cl$^-$ ion) was used as a test solution.

(5) Procedures of Electrophoresis

The sample for migration and the test solution were introduced in the same way as in Example 1, and after concentrating by ITP and carrying out CGE, an intensity of fluorescence generated by 635 nm laser excitation in the capillary part 2 cm apart from the LB2 channel crossing part was measured over time using a fluorescence microscope (BX-50, manufactured by Olympus Co., Ltd.).

[Results]

Figure 5:
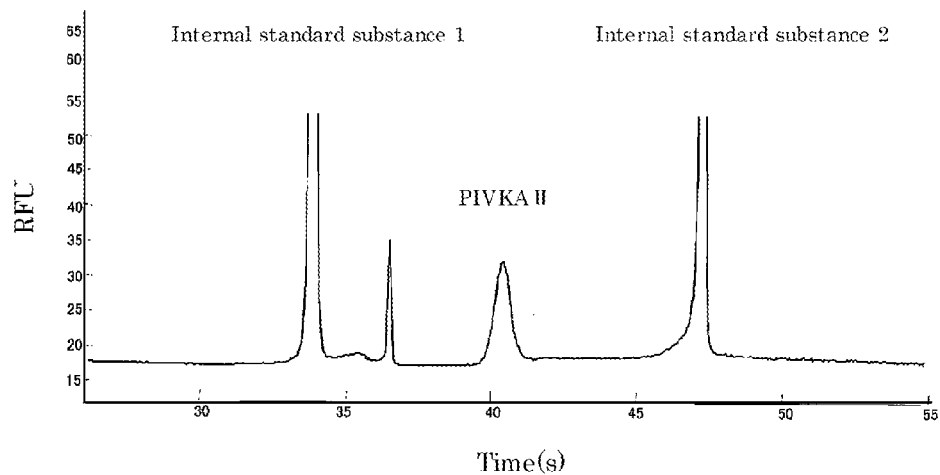
FIG. 5 is an electropherogram when PIVKA II was measured by the method of the present invention in Example 1.

An electrophoretic profile (electropherogram) when the sample for migration was used is shown in FIG. 5. It should be noted that in FIG. 5, the vertical axis represents fluorescence intensity, and the horizontal axis represents retention time, respectively.

From the above-described results, it was found that by carrying out electrophoresis using internal standard substances 1 and 2 relevant to the present invention, a peak of PIVKA II was allowed to be positioned between both peaks of the internal standard substances, and thereby the peak of PIVKA II could be identified easily.

The invention claimed is:

1. A measurement method for an analyte by a capillary electrophoresis method, comprising:

identifying a peak of the analyte with an internal standard substance which is a combination of a compound I, and a compound II, wherein the compound I is a compound represented by the general formula [1] or a salt thereof:

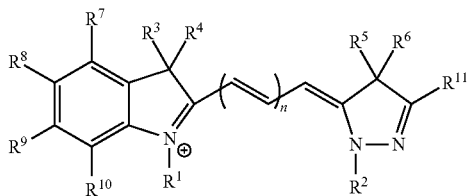

[1]

wherein $R^1$ to $R^6$ each independently represent an alkyl group having —COO⁻ or —SO₃⁻ as a substituent or being unsubstituted, and optionally having an amide bond;

wherein $R^7$ to $R^{10}$ each independently represent an alkyl group, an alkynyl group, an aryl group, an alkoxy group, an aryloxy group, an alkylsulfonyl group, an arylsulfonyl group, a substituted amino group, —COO⁻, —SO₃⁻, a halogen atom, a hydrogen atom, a hydroxyl group, a cyano group or a nitro group;

wherein $R^{11}$ represents a hydrogen atom, an alkyl group, an alkynyl group or an aryl group, and n represents an integer from 0 to 3, and wherein at least 3 groups of $R^1$ to $R^{10}$ are —COO⁻, —SO₃⁻, or groups having —COO⁻ or —SO₃ as a substituent; and wherein the compound II is a compound II' represented by the general formula [1'] or a salt thereof:

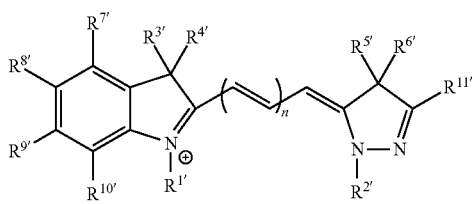

[1']

wherein compound II has a same skeleton as compound I, except that 1 to 3 anion groups are substituted by cation groups represented by the following general formula [103]:

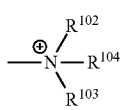

[103]

wherein $R^{1'}$ to $R^{6'}$ each independently represent either (i) an alkyl group having —COO⁻ or —SO₃⁻ as a substituent or being unsubstituted, the alkyl group optionally having an amide bond, or (ii) an alkyl group having a group represented by the general formula [101] as a substituent:

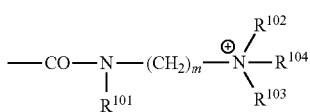

[101]

wherein $R^{101}$ to $R^{104}$ each independently represent a hydrogen atom or an alkyl group of $C_1$ to $C_3$;

wherein m represents an integer from 2 to 6; and wherein 2 to 3 groups of $R^{102}$ to $R^{104}$ together with a nitrogen atom to which they are bound may form a heterocyclic ammonium cation, wherein $R^{7'}$ to $R^{10'}$ each independently represent an alkyl group, an alkynyl group, an aryl group, an alkoxy group, an aryloxy group, an alkylsulfonyl group, an arylsulfonyl group, a substituted amino group, —COO⁻, —SO₃⁻, a halogen atom, a hydroxyl group, a cyano group or a nitro group;

wherein $R^{11'}$ represents a hydrogen atom, an alkyl group, an alkynyl group or an aryl group; and n represents an integer from 0 to 3, and wherein at least one of $R^{1'}$ to $R^{6'}$ is an alkyl group having a group represented by the general formula [101] as a substituent.

2. The measurement method according to claim 1, wherein $R^7$ to $R^{10}$ each independently represent —COO⁻, —SO₃⁻ or a hydrogen atom;

wherein $R^{11}$ represents an alkyl group; and wherein $R^{7'}$ to $R^{10'}$ each independently represent —COO⁻, —SO₃⁻ or a hydrogen atom; and wherein $R^{11'}$ represents an alkyl group.

3. The measurement method according to claim 2, wherein $R^1$ and $R^2$ each independently represent an alkyl group having —COO⁻ or —SO₃⁻ as a substituent;

wherein either one of $R^3$ and $R^4$ represents an alkyl group having —COO⁻ or —SO₃⁻ as a substituent, and the other one of $R^3$ and $R^4$ represents an unsubstituted alkyl group;

wherein either one of $R^5$ and $R^6$ represents an alkyl group having —COO⁻ or —SO₃⁻ as a substituent, and the other one of $R^5$ and $R^6$ represents an unsubstituted alkyl group.

4. The measurement method according to claim 2, wherein either one of $R^{1'}$ and $R^{2'}$ represents an alkyl group having —COO⁻ or —SO₃⁻ as a substituent, and the other one of $R^{1'}$ and $R^{2'}$ represents an alkyl group having, as a substituent, a group represented by the general formula [101];

wherein either one of $R^{3'}$ and $R^{4'}$ represents an alkyl group having —COO⁻ or —SO₃⁻ as a substituent, and the other one of $R^{3'}$ and $R^{4'}$ represents an unsubstituted alkyl group; and wherein either one of $R^{5'}$ and $R^{6'}$ represents an alkyl group having —COO⁻ or —SO₃⁻ as a substituent, and the other one of $R^{5'}$ and $R^{6'}$ represents an unsubstituted alkyl group.

5. The measurement method according to claim 1, wherein the analyte is AFP or PIVKA II.

6. The measurement method according to claim 2, wherein the analyte is AFP or PIVKA II.

7. The measurement method according to claim 3, wherein the analyte is AFP or PIVKA II.

8. The measurement method according to claim 4, wherein the analyte is AFP or PIVKA II.

* * * * *